(12) United States Patent
Imai et al.

(10) Patent No.: US 10,563,241 B2
(45) Date of Patent: Feb. 18, 2020

(54) BIOSENSOR

(71) Applicant: KABUSHIKI KAISHA TOSHIBA, Minato-ku, Tokyo (JP)

(72) Inventors: Kaita Imai, Tokyo (JP); Shouhei Kousai, Yokohama Kanagawa (JP); Soichiro Ueno, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 317 days.

(21) Appl. No.: 15/633,720

(22) Filed: Jun. 26, 2017

(65) Prior Publication Data

US 2017/0306383 A1 Oct. 26, 2017

Related U.S. Application Data

(63) Continuation of application No. PCT/JP2015/085855, filed on Dec. 22, 2015.

(30) Foreign Application Priority Data

Dec. 26, 2014 (JP) ................................. 2014-265521

(51) Int. Cl.
*G01N 27/327* (2006.01)
*C12Q 1/00* (2006.01)
(Continued)

(52) U.S. Cl.
CPC ............... *C12Q 1/001* (2013.01); *A01N 1/02* (2013.01); *G01N 27/26* (2013.01); *G01N 27/305* (2013.01); *G01N 27/327* (2013.01); *G01N 33/4836* (2013.01); *B82Y 30/00* (2013.01); *C12Q 1/00* (2013.01); *G01N 21/64* (2013.01);
(Continued)

(58) Field of Classification Search
CPC ............ G01N 27/305; G01N 33/4836; G01N 2223/501; G01N 2291/106; G01N 2201/0833; G01N 2201/1085
See application file for complete search history.

(56) References Cited

U.S. PATENT DOCUMENTS 4,865,716 A * 9/1989 Sibbald ................ G01N 27/414
204/409
5,120,421 A * 6/1992 Glass .................... G01N 27/27
204/400

(Continued)

FOREIGN PATENT DOCUMENTS

CN 103630571 A 3/2014
JP 08062209 A 3/1996
(Continued)

OTHER PUBLICATIONS

International Search Report (ISR) and Written Opinion dated Mar. 15, 2016 issued in International Application No. PCT/JP2015/085855.

(Continued)

*Primary Examiner* — Alexander S Noguerola
(74) *Attorney, Agent, or Firm* — Holtz, Holtz & Volek PC

(57) ABSTRACT

According to one embodiment, a biosensor includes a substrate and a sensor matrix that is present in a two-dimensional region on the substrate. The sensor matrix includes a plurality of basic blocks. Each of the basic blocks includes at least three types of sensor elements.

12 Claims, 21 Drawing Sheets

(51) Int. Cl.
*G01N 33/483* (2006.01)
*G01N 27/30* (2006.01)
*A01N 1/02* (2006.01)
*G01N 27/26* (2006.01)
*G01N 21/64* (2006.01)
*G01N 21/76* (2006.01)
*B82Y 30/00* (2011.01)

(52) U.S. Cl.
CPC ..... *G01N 21/763* (2013.01); *G01N 2223/501* (2013.01); *G01N 2291/106* (2013.01)

(56) References Cited

U.S. PATENT DOCUMENTS

| | | | |
|---|---|---|---|
| 5,563,067 | A | 10/1996 | Sugihara et al. |
| 6,297,025 | B1 | 10/2001 | Sugihara et al. |
| 6,890,762 | B1 | 5/2005 | Sugihara et al. |
| 7,851,184 | B2 * | 12/2010 | Pollack ............... C12Q 1/6869 435/6.11 |
| 2009/0093376 | A1 | 4/2009 | Wo et al. |
| 2011/0279901 | A1 | 11/2011 | Watanabe |
| 2011/0291643 | A1 | 12/2011 | Ravindran et al. |
| 2012/0103836 | A1 * | 5/2012 | Hori ..................... G01N 27/305 205/792 |
| 2013/0274126 | A1 | 10/2013 | Ishige et al. |
| 2014/0139204 | A1 * | 5/2014 | Bashir .................... G01N 33/84 324/123 R |

FOREIGN PATENT DOCUMENTS

| | | |
|---|---|---|
| JP | 2000055874 A | 2/2000 |
| JP | 3204875 B2 | 9/2001 |
| JP | 2003083932 A | 3/2003 |
| JP | 2004028723 A | 1/2004 |
| JP | 2007248994 A | 9/2007 |
| JP | 4133028 B2 | 8/2008 |
| JP | 4137239 B2 | 8/2008 |
| JP | 2009276976 A | 11/2009 |
| JP | 2010039659 A | 2/2010 |
| JP | 4825976 B2 | 11/2011 |
| JP | 2011242437 A | 12/2011 |
| JP | 2012013579 A | 1/2012 |
| JP | 4910127 B2 | 4/2012 |
| JP | 2012073191 A | 4/2012 |
| JP | 2012095803 A | 5/2012 |
| JP | 2012207991 A | 10/2012 |
| JP | 2013220066 A | 10/2013 |
| TW | 200916752 A | 4/2009 |

OTHER PUBLICATIONS

K. Atsumi, et al., "2-Dimensional Potassium Ion Image Sensor Aiming for Label-Free Dynamic Imaging of Living-Cell Activity," 2009 International Solid-State Sensors, Actuators and Microsystems Conference (Transducers 2009), Jun. 21-25, 2009, pp. 916-919.
M. Ballini, et al., "A 1024-Channel CMOS Microelectrode-Array System with 26'400 Electrodes for Recording and Stimulation of Electro-active Cells In-vitro," 2013 Symposium on VLSI Circuits (VLSIC) Digest of Technical Papers, Jun. 12-14, 2013, pp. C54-C55.
M. Beiderman, et al., "A Low-Light CMOS Contact Imager With an Emission Filter for Biosensing Applications," IEEE Transactions on Biomedical Circuits and Systems, vol. 2, No. 3, Sep. 2008, pp. 193-203.
L. Blockstein, et al., "A PVAc-Based Benzophenone-8 Filter as an Alternative to Commercially Available Dichroic Filters for Monitoring Calcium Activity in Live Neurons via Fura-2 AM," IEEE Photonics Journal, vol. 4, No. 3, May 22, 2012, pp. 1004-1012.
B. Eversmann, et al., "A 128×128 CMOS Biosensor Array for Extracellular Recording of Neural Activity," IEEE Journal of Solid-State Circuits, vol. 38, No. 12, Dec. 2003, pp. 2306-2317.

A. Hierlemann, et al., "Growing Cells Atop Microelectronic Chips: Interfacing Electrogenic Cells In Vitro With CMOS-Based Microelectrode Arrays," Proceedings of the IEEE, vol. 99, No. 2, Feb. 2011, pp. 252-284.
T. Hizawa, et al., "Characteristics of Highly Sensitive pH Sensors with Charge Accumulation Operation," Japanese Journal of Applied Physics, vol. 45, No. 12, 2006, pp. 9259-9263.
X. Huang, et al., "A 64×64 1200fps CMOS Ion-Image Sensor with Suppressed Fixed-Pattern-Noise for Accurate High-throughput DNA Sequencing," 2014 Symposium on VLSI Circuits Digest of Technical Papers, Jun. 10-13, 2014, pp. 134-135.
H. M. Jafari, et al., "Nanostructured CMOS Wireless Ultra-Wideband Label-free DNA Analysis SoC," 2012 Symposium on VLSI Circuits Digest of Technical Papers, Jun. 13-15, 2012, pp. 122-123.
B. Jang, et al., "A CMOS Fluorescent-Based Biosensor Microarray," 2009 IEEE International Solid-State Circuits Conference—Digest of Technical Papers (ISSCC 2009), Feb. 8-12, 2009, pp. 436-437, 437a.
H. Ji, et al., "Contact Imaging: Simulation and Experiment," IEEE Transactions on Circuits and Systems—I: Regular Papers, vol. 54, No. 8, Aug. 2007, pp. 1698-1710.
B. Johnson, et al., "A 768-Channel CMOS Microelectrode Array With Angle Sensitive Pixels for Neuronal Recording," IEEE Sensors Journal, vol. 13, No. 9, Sep. 2013, pp. 3211-3218.
K.W. Kao, et al., "Calcium Ions Detection Using Miniaturized INN-Based Sensor," 2012 IEEE 25th International Conference on Micro Electro Mechanical Systems (MEMS 2012), Jan. 29-Feb. 2, 2012, pp. 781-783.
A. Kono, et al., "Real-Time Analysis of Glutamate Regulated Function in Neurons Using Label-Free Potassium Imaging System," Transducers 2013, Jun. 16-20, 2013, pp. 361-364.
N. Manaresi, et al., "A CMOS Chip for Individual Cell Manipulation and Detection," IEEE Journal of Solid-State Circuits, vol. 38, No. 12, Dec. 2003, pp. 2297-2305.
J. Matsuo, et al., "Multimodal pH and Light Imaging Devices for Dynamic Chemical Reaction Observation," Twelfth International Conference on Miniaturized Systems for Chemistry and Life Sciences, Oct. 12-16, 2008, pp. 326-328.
M. Milgrew, et al., "A 16×16 CMOS Proton Camera Array for Direct Extracellular Imaging of Hydrogen-Ion Activity," 2008 IEEE International Solid-State Circuits Conference, Feb. 6, 2008, pp. 590-591, 638.
A. K. Mudraboyina, et al., "A Novel Lensless Miniature Contact Imaging System for Monitoring Calcium Changes in Live Neurons," IEEE Photonics Journal, vol. 6, No. 1, Feb. 4, 2014.
H. Nakazawa, et al., "High-Sensitivity Charge-Transfer-Type pH Sensor With Quasi-Signal Removal Structure," IEEE Transactions on Electron Devices, vol. 61, No. 1, Jan. 2014, pp. 136-140.
H. Nakazawa, et al., "Multimodal Proton and Fluorescence Image Sensor for Bio Applications," 2011 IEEE/IFIP 19th International Conference on VLSI and System-on-Chip, Oct. 3-5, 2011, pp. 5-9.
H. Nakazawa, et al., "Reduction of Interference Between pH and Optical Output Signals in a Multimodal Bio-Image Sensor," IEEE Sensors Journal, vol. 11, No. 11, Nov. 2011, pp. 2718-2722.
A. Romani, et al., "Capacitive Sensor Array for Localization of Bioparticles in CMOS Lab-on-a-Chip," 2004 IEEE International Solid-State Circuits Conference, Feb. 15-19, 2004.
R. R. Singh, et al., "A CMOS-Microfluidic Chemiluminescence Contact Imaging Microsystem," IEEE Journal of Solid-State Circuits, vol. 47, No. 11, Nov. 2012, pp. 2822-2833.
R. R. Singh, et al., "A CMOS/Thin-Film Fluorescence Contact Imaging Microsystem for DNA Analysis," IEEE Transactions on Circuits and Systems—I: Regular Papers, vol. 57, No. 5, May 2010, pp. 1029-1038.
H. Takehara, et al., "A CMOS image sensor with stacked photodiodes for lensless observation system of digital enzyme-linked immunosorbent assay," Japanese Journal of Applied Physics, vol. 53, No. 4S, Feb. 17, 2014, pp. 04EL02-1 to 04EL02-5.
S. Takenaga, et al., "Charge Accumulation Type Hydrogen Ion Image Sensor with High pH Resolution," Japanese Journal of Applied Physics, vol. 50, No. 2R, Feb. 21, 2011, pp. 027001-1 to 027001-5.

(56) References Cited

OTHER PUBLICATIONS

S. Takenaga, et al., "Label-Free Acetylcholine Image Sensor Based on Charge Transfer Technology for Biological Phenomenon Tracking," Japanese Journal of Applied Physics, vol. 51, No. 2R, Jan. 23, 2012, pp. 027001-1 to 027001-5.

T. Tokuda, et al., "An optical and potential dual-image CMOS sensor for on-chip neural and DNA imaging applications," 2006 IEEE International Symposium on Circuits and Systems, May 21-24, 2006, pp. 1127-1130.

T. Tokuda, et al., "Optical and electrochemical dual-image CMOS sensor for on-chip biomolecular sensing applications", Sensors and Actuators A: Physical, vol. 135, No. 2, 2007, pp. 315-322.

T. Yamazaki, et al., "Smart Integrated Sensor for Multiple Detections of Glucose and L-Lactate Using On-Chip Electrochemical System," Journal of Sensors, vol. 2011, 7 pages.

Dojindo Laboratories, "I Want to Measure the Ion Concentration with an Electrode," Jul. 8, 2014, pp. 107-109, http://www.dojindo.co.jp/technical/protocol/p38.pdf.

\* cited by examiner

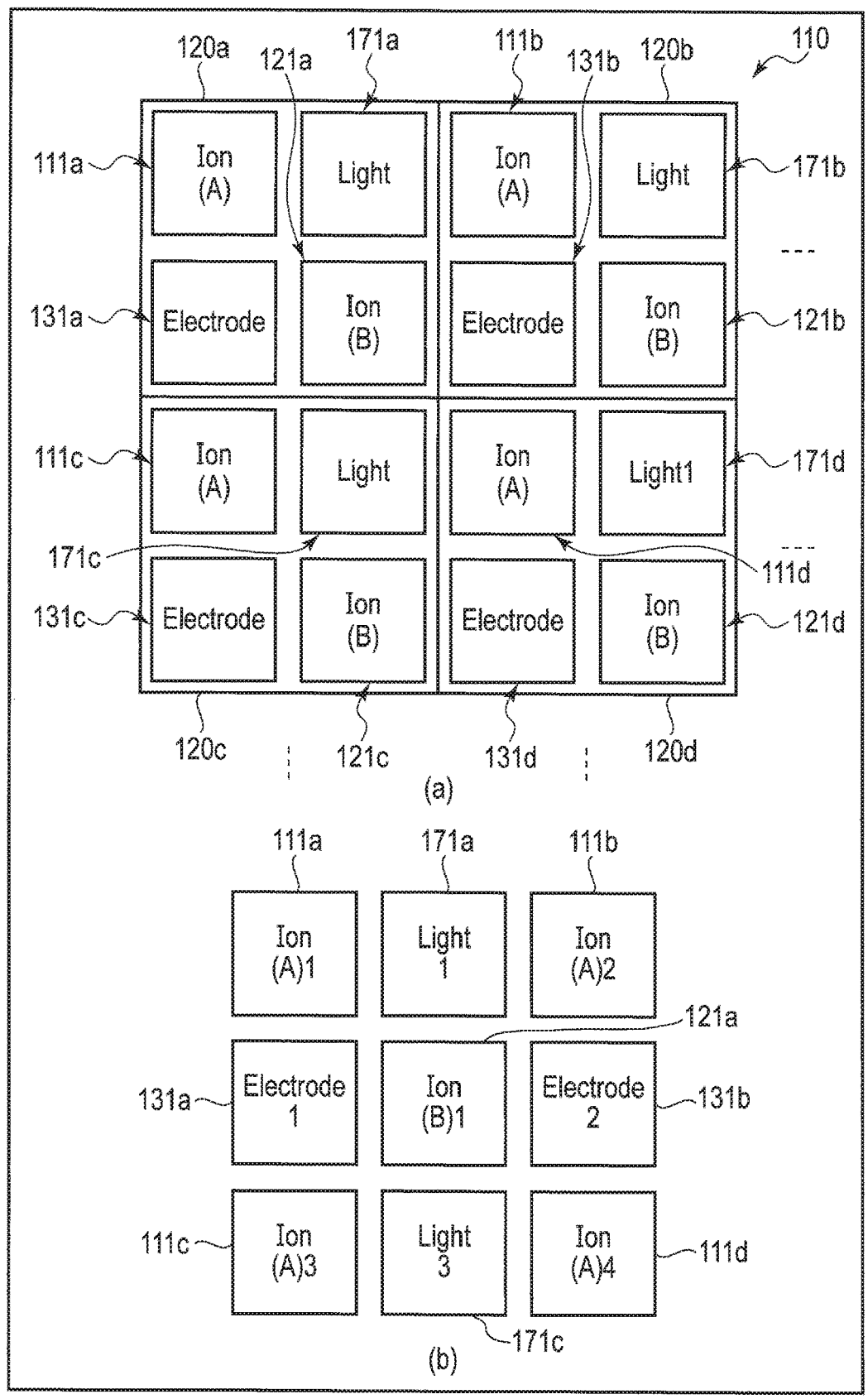
F I G. 1

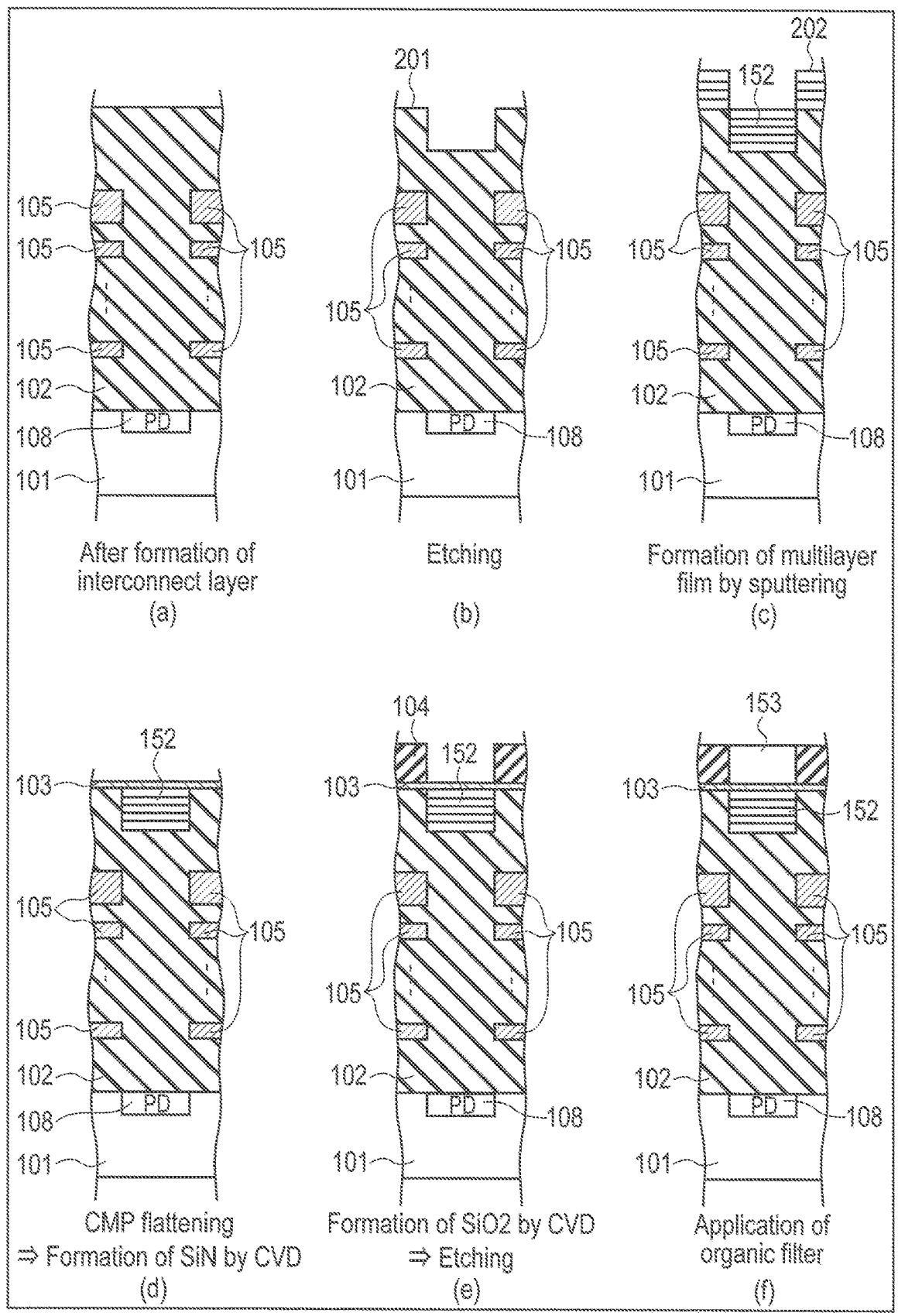
F I G. 4

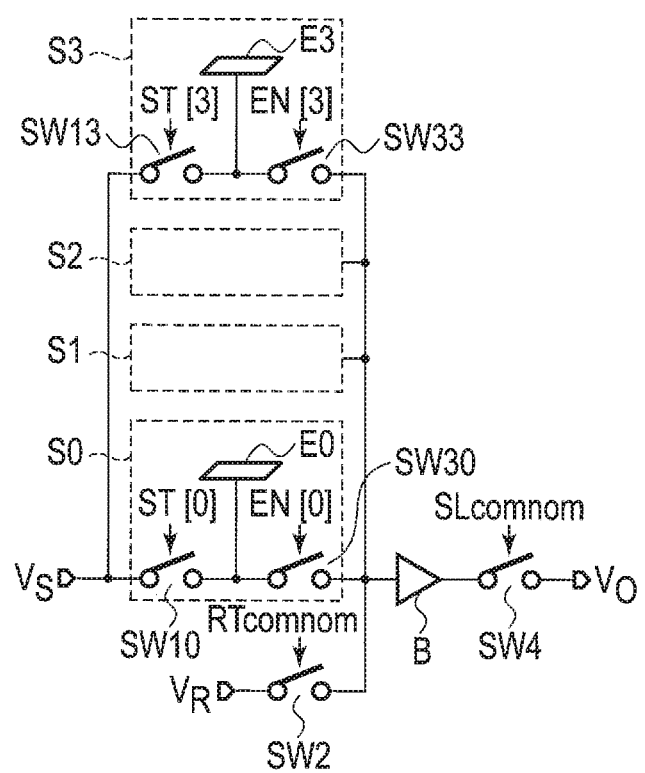
F I G. 14

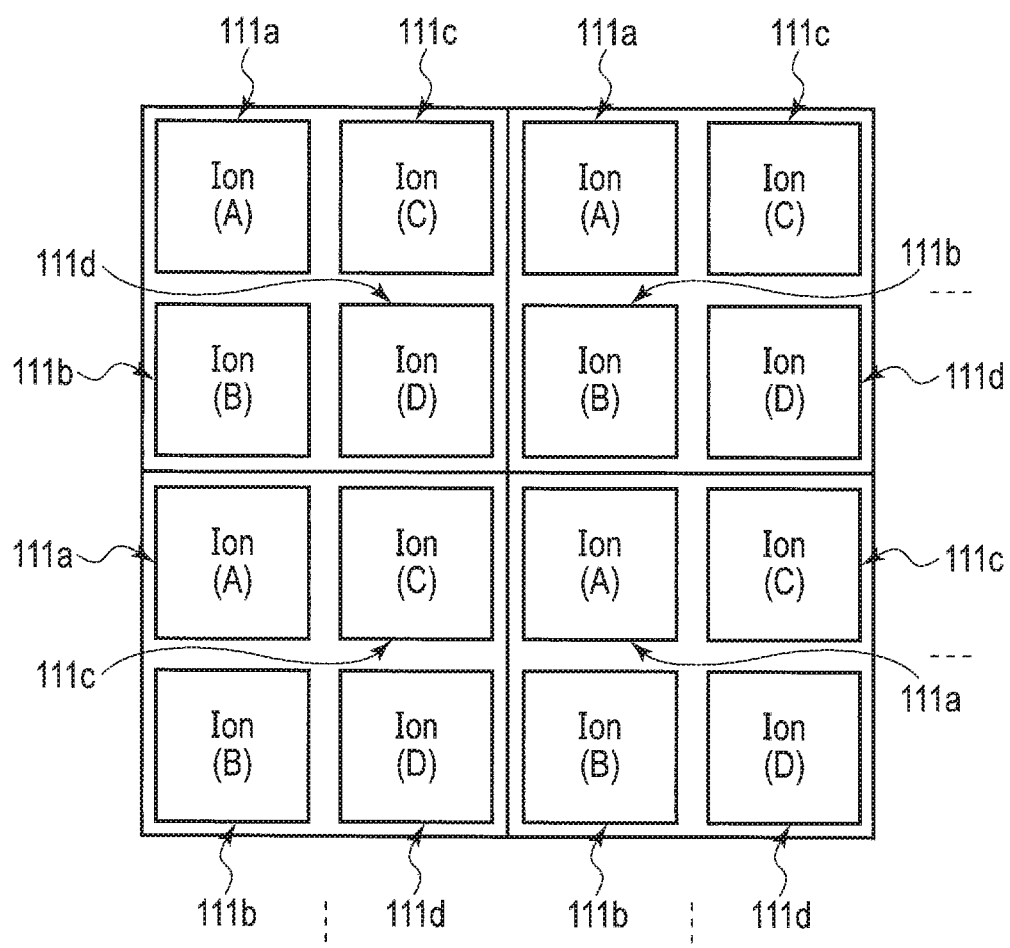
F I G. 16

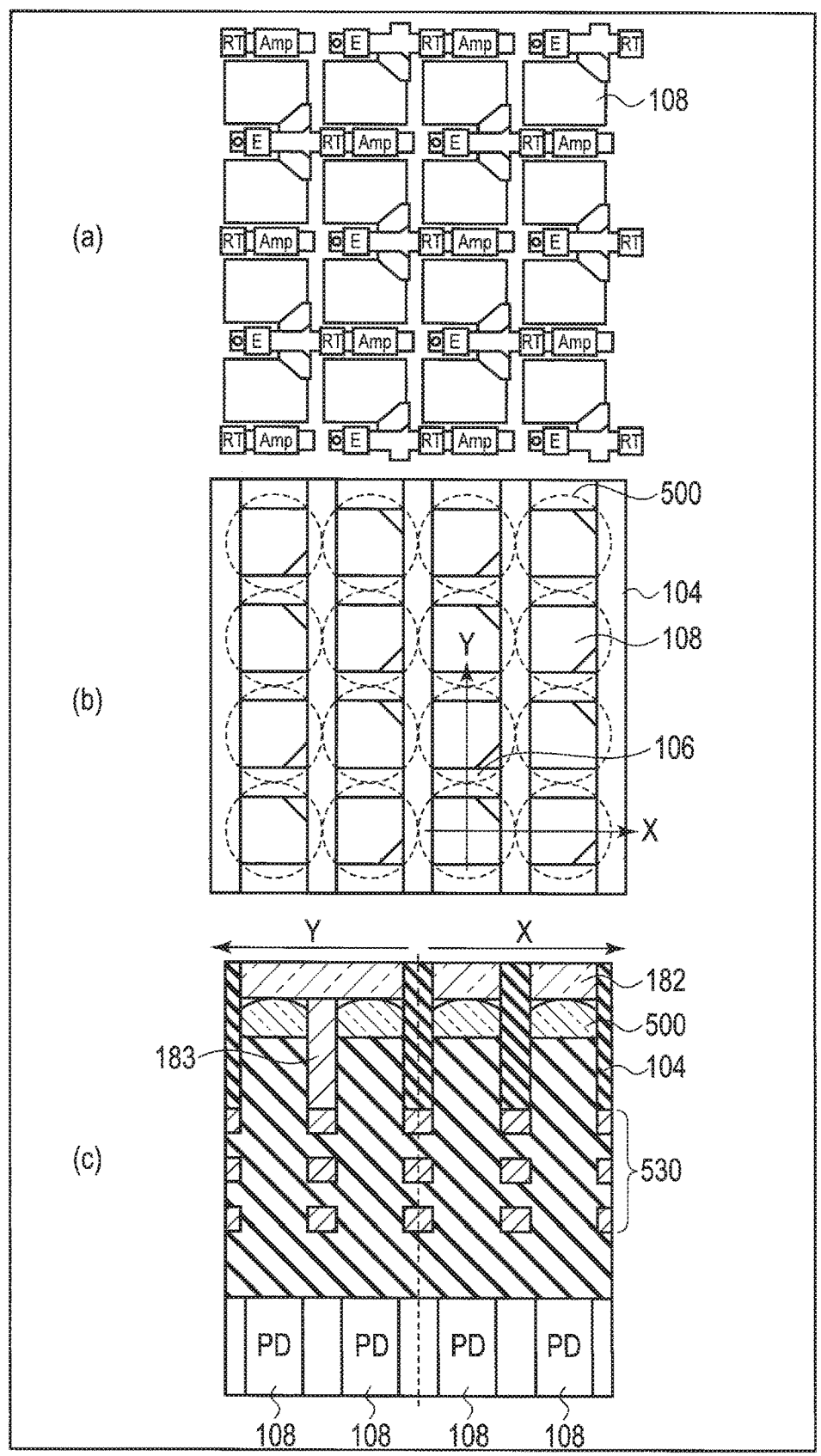
F I G. 25

BIOSENSOR

CROSS-REFERENCE TO RELATED APPLICATIONS

This application is a Continuation Application of PCT Application No. PCT/JP2015/085855, filed Dec. 22, 2015 and based upon and claiming the benefit of priority from Japanese Patent Application No. 2014-265521, filed Dec. 26, 2014, the entire contents of all of which are incorporated herein by reference.

FIELD

Embodiments described herein relate generally to a biosensor.

BACKGROUND

Recently, various types of biosensors to perform biomeasurement on a semiconductor chip are developed. Examples of the biosensor include a biosensor that measures an ion concentration, a biosensor that measures light, a biosensor that observes the chemical behavior of a test substance by measuring the fluorescence intensity, and a biosensor that observes the activity of cells by measuring the electric potential.

On the other hand, in order to achieve a social system that enables people to live healthily and comfortably, studies to reveal causes and pathogenic mechanisms of the diseases and studies related to preventing or curing methods based on the above studies have been performed. Further, in order to reduce the risk of developing diseases, it has been suggested to collect and analyze information on the diseases revealed by the studies and information such as pathogenic factors in individuals, for example, congenital, postnatal, and lifestyle factors.

In such circumstances, there is a need for further development of the biosensor.

BRIEF DESCRIPTION OF THE DRAWINGS

FIG. 1 is plan view showing an example of a biosensor according to an embodiment.

FIG. 4 is cross-sectional view showing an example of a production process of a photosensor pixel of the biosensor according to the embodiment.

FIG. 14 is a circuit diagram showing an example of each subblock of the biosensor according to the embodiment.

FIG. 16 is a plan view showing an example of a sensor array according to an embodiment.

FIG. 25 is view showing an example of a biosensor according to an embodiment.

DETAILED DESCRIPTION

Figure 2:
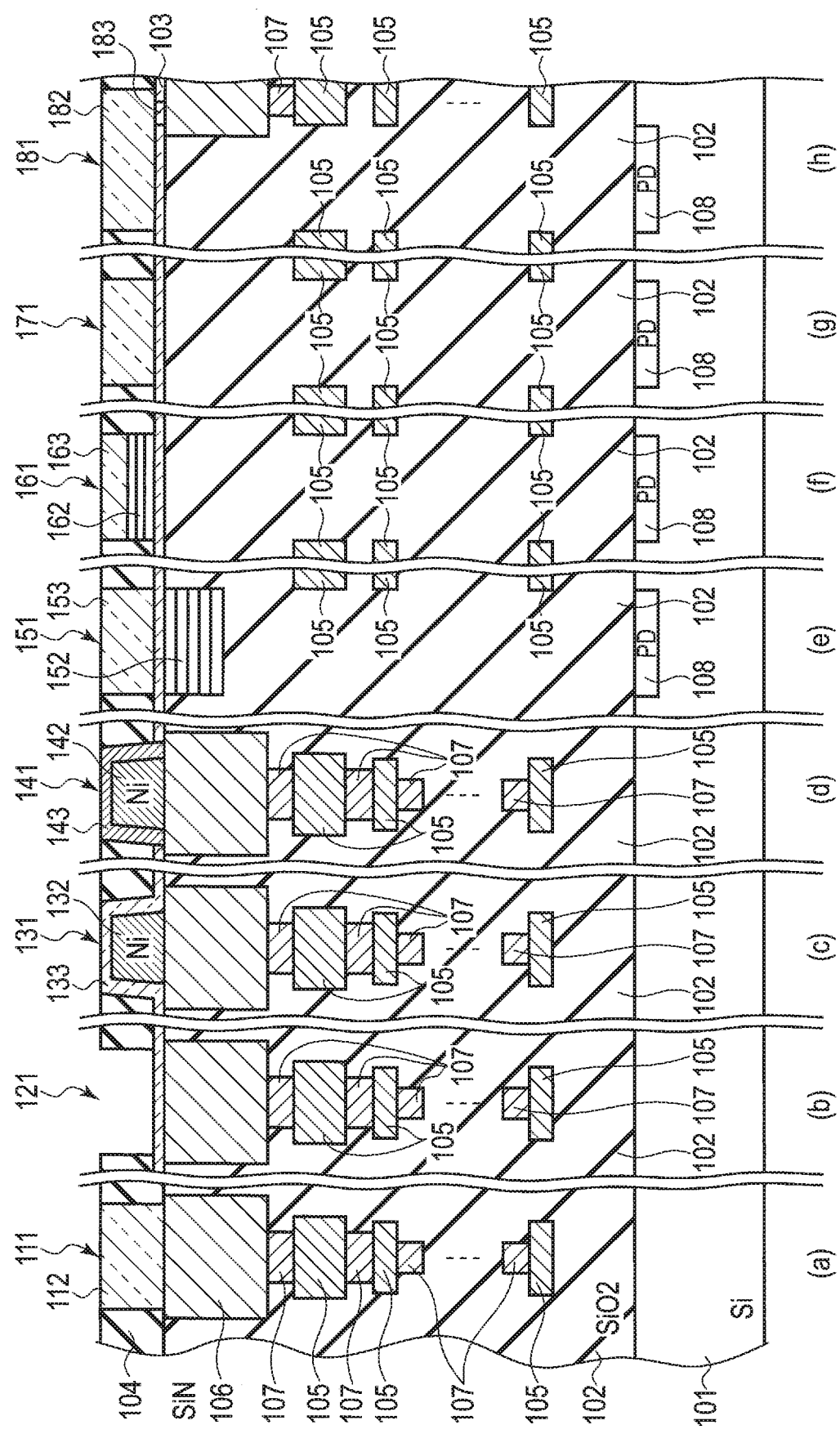
FIG. 2 is cross-sectional view showing an example of a sensor pixel of the biosensor according to the embodiment.

In general, according to one embodiment, a biosensor includes a substrate and a sensor matrix present in a two dimensional region on the substrate. The sensor matrix includes a plurality of basic blocks. Each of the basic blocks includes at least three types of sensor elements.

The sensor elements include sensing units. All the sensing units in the sensor matrix face the one surface side of the biosensor. In other words, each of the sensing units is exposed to the outside of one surface of the biosensor. All the sensing units of all the sensor elements in the sensor matrix of the biosensor form a sensor pixel array as a whole. That is, the result obtained by the biosensor may be an image which includes information from each of the sensing units as a pixel.

An example of the biosensor will be described with reference to FIG. 1(a). FIG. 1(a) is an image view showing a part of the surface of the substrate on which the sensing units of the biosensor are disposed. The sensor matrix is an array including a plurality of sensor pixels, i.e., a sensor pixel array.

It is illustrated herein that at least four sensor pixels $120a$, $120b$, $120c$, and $120d$ are disposed in a row on a sensor matrix 110. Each of the sensor pixels is configured to include a basic block. In a basic block, four types of sensor elements are arranged in a matrix. Specifically, the sensor elements are disposed in two rows and two columns. Thus, each of the sensor pixels includes four types of sensing units arranged in a matrix form. Each of the sensing units is a sensor pixel as a subpixel.

Two of the four sensing units shown in FIG. 1(a) are ion sensing units $111a$, $111b$, $111c$, and $111d$ and ion sensing units $121a$, $121b$, $121c$, and $121d$, which measure different ion concentrations, (as shown as "Ion (A)" and "Ion (B)" in FIG. 1(a)). The rest of the two sensing units are electrical sensing units 131a, 131b, 131c, and 131d ("Electrode" in FIG. 1(a)) and optical sensing units 171a, 171b, 171c, and 171d ("Light" in FIG. 1(a)).

The biosensor having such a configuration allows for simultaneous detection of concentrations of two types of ions, an electrical signal, and a light signal.

According to the biosensor of the embodiment, it is possible to simultaneously detect a plurality of items on an analysis target, whereby it is possible to perform the test more rapidly. Further, it is possible to comprehensively analyze a sample to be examined based on the results obtained from the plurality of items, which enables a more accurate analysis result to be obtained. That is, according to the biosensor of the embodiment, it is possible to obtain information on a plurality of test items (multiple items) with high reliability.

FIG. 1(a) shows an example in which the basic block includes four sensor elements arranged in a matrix of 2×2. As described above, each of the sensing units included in the sensor pixel is a subpixel, while each of the sensor elements is a subblock based on the basic block. The characteristic of the biosensor having the basic block is that twice the pitch of each subblock is the pitch of the basic block. As an example, focusing on the sensing unit 121a (Ion (B)), when obtaining the detection result from the sensing unit 121a (Ion (B)) in the whole sensor pixel array, regions where signals cannot be directly obtained are formed since other types of subblocks are disposed. The information on these regions can be interpolated using, for example, information on sensing units (e.g., the sensing units 111a, 111b, 111c, and 111d (Ions (A)) which surround the sensing unit 121a (Ion (B)). Thus, the resolution can be improved.

FIG. 1(b) shows an example thereof. In the case where a value is interpolated in order to obtain a concentration value of Ion (A) in the position of the sensing unit (Ion (B)), the value can be interpolated according to the following formula using concentration values obtained from Ion (A) (the sensing units 111a ("Ion (A) 1" in FIG. 1(b)), 111b ("Ion (A) 2" in FIG. 1(b)), 111c ("Ion (A) 3" in FIG. 1(b)), 111d ("Ion (A) 4" in FIG. 1(b)). Similarly, concentration values obtained from the sensing units 111a, 111b, 111c, and 111d (Ions (A)) are used to interpolate values of the electrical sensing units 131a and 131b ("Electrode 1" and "Electrode 2" in FIG. 1(b)) and the optical sensing units 171a and 171c ("Light 1", "Light 3" in FIG. 1(b)) located among those sensing units.

Interpolated value of Ion (A) in the position of Ion (B) 1=([Ion (A) 1]+[Ion (A) 2]+[Ion (A) 3]+[Ion (A) 4])/4

Interpolated value of Ion (A) in the position of Electrode 1=([Ion (A) 1+ion (A) 3])/2

Interpolated value of Ion (A) in the position of Electrode 2=([Ion (A) 2]+Ion (A) 4)/2

Interpolated value of Ion (A) in the position of Light 1=([Ion (A) 1]+[Ion (A) 2])/2

Interpolated value of Ion (A) in the position of Light 3=([Ion (A) 3]+[Ion (A) 4])/2

Such interpolation allows for measurement with high resolution.

The basic block including four sensor elements of 2×2 matrix is described above, however it is not limited thereto. The number of the sensor elements included in the basic block and the number of the row or column of the matrix may be arbitrarily selected.

The size of each of the sensor pixels may be, for example, in a range of from 300 nm×300 nm to 20 µm×20 µm, in a range of from 300 nm×300 nm to 10 µm×10 µm or in a range of from 300 nm×300 nm to 1 µm×1 µm. For example, the size of the sensing unit in a basic block may be changed depending on the type of sensor element. Alternatively, the size of the sensing unit may be determined, for example, depending on the size of the signal to be sensed. The pitch between the sensor subpixels may be, for example, from 0.5 µm to 30 µm, however it is not limited thereto. For example, in order to measure the visible light, the pitch between visible light sensor subpixels is sufficient if it is one half of the wavelength in a visible light region.

A sensor element which may be included in the biosensor may be a sensor element in which the sensing unit is capable of sensing information on at least one selected from the group consisting of a chemical substance dependent signal, a light signal, e.g., visible light, ultraviolet light, near infrared, infrared light, fluorescence, phosphorescence, bioluminescence, temperature, and an electrical signal. Further, the biosensor includes at least three types of sensor elements. As an example, in the case where the biosensor includes three types of sensor elements, the sensor element may be a combination of any of the three types of sensor elements. Alternatively, the combination of the sensor elements may be a combination of three types of sensor elements which measure different chemical substances or a combination of three types of sensor elements which measure the visible light and/or fluorescence having different wavelengths. A sensor element may co-sense information on at least two types selected from the above signals. In other words, at least three types of sensor elements to be used in the biosensor may be at least three sensor elements having different functions.

The sensor element that detects a chemical substance by the sensing unit may be, for example, a chemical sensor element. The sensor element that detects visible light and/or fluorescence by the sensing unit may be, for example, a photosensor element. The sensor element that detects an electrical signal by the sensing unit may be, for example, an electrical sensor element. Further, the electrical sensor element may be a sensor element that measures current, voltage or impedance. The sensor element that detects the temperature by the sensing unit may be, for example, a temperature sensor element. Alternatively, the pixel that senses the temperature (i.e., a temperature measuring pixel) is not provided as an independent temperature sensor element, but may be provided after being incorporated into any of configurations of the biosensor, such as another sensor element, a chemical sensor element, a photosensor element and/or an electrical sensor element or a region that surrounds the pixels of these elements. In that case, the sensor element having a temperature sensor function may be a temperature sensor element.

For example, the signal detected by the biosensor may be a cell signal from a target to be measured. The "information to be detected" may include light information, ion information, electrical information, temperature, other information, and the like. The light information includes, for example, light intensity, fluorescence intensity, bioluminescence intensity, phosphorescence intensity, and autofluorescence intensity, and the like. The electrical information includes, for example, potential, current, voltage, and impedance, and the like. Such information may include time-dependent changes in desired items. The type of the sensor element is selected depending on the information to be detected.

The basic block includes at least three types of sensor elements depending on the information to be detected. The sensor element included in the basic block may be, for example, a photosensor element, a chemical sensor element and/or an electrical sensor element.

The photosensor element obtains light information on the target to be measured which is sensed by the photosensor element. The light information is information on any light obtained by irradiating the target to be measured with light. The photosensor element may be a semiconductor element that senses a light signal and converts the signal to an electrical signal. The light sensed may be visible light, ultraviolet light, infrared light, fluorescence, phosphorescence, luminescence or the like. Thus, it is possible to obtain morphological information on the target to be measured, distribution of the target to be measured, and information on the distribution, concentration, and behavior of the substance related to the target to be measured.

Examples of the photosensor element may include a CMOS image sensor that converts the light detected by a photodiode into an electrical signal, a single-photon avalanche diode (SPAD) image sensor that converts the light detected by SPAD into an electrical signal, an image sensor that uses a solid-state image sensor element such as a CCD image sensor, and a sensor that uses a thermoelectric conversion element such as a thermopile sensor.

The chemical sensor element may be a semiconductor sensor element that senses a characteristic or change of a chemical substance and converts it into an electrical signal. Thus, the chemical sensor element detects physical, chemical, and biochemical changes in the chemical substance. The chemical sensor element is a semiconductor sensor element that senses an ion such as H+, K+ or Ca2+, a neurotransmitter such as acetylcholine, a metabolite such as a metabolic product or a substance being metabolized formed extracellularly or intracellularly, a specific antigen or antibody, or a protein derived therefrom, and converts a signal based on information from the chemical substance to be detected into an electrical signal. Examples of the chemical sensor element may or chemical field-effect transistors, ISFETs, and CHEMFETs.

The electrical sensor element is a semiconductor element that obtains electrical information on the target to be measured. The electrical sensor element may be a semiconductor element which senses a potential, a current, a voltage or an impedance in order to detect potential information such as action potential of cells, the ground level of cells, the adhesion and contact between cells, and the activation and activated state of target substances to be measured (such as cells) and which produces a current or voltage signal. The production of a current or voltage signal induces the stimulation, activation or inactivation of the target substances to be measured. Further, the sensor element may be a temperature sensor element. The sensing of each of the elements and the conversion of the information obtained by the sensing into an electrical signal may be performed under control of a control system. Furthermore, a sensor element for detecting other substances may be included. Examples of the electrical sensor element may include a semiconductor sensor that uses an electrode and a semiconductor voltage sensor.

Subsequently, the configuration of each of the sensor elements will be described in detail.

Figure 3:
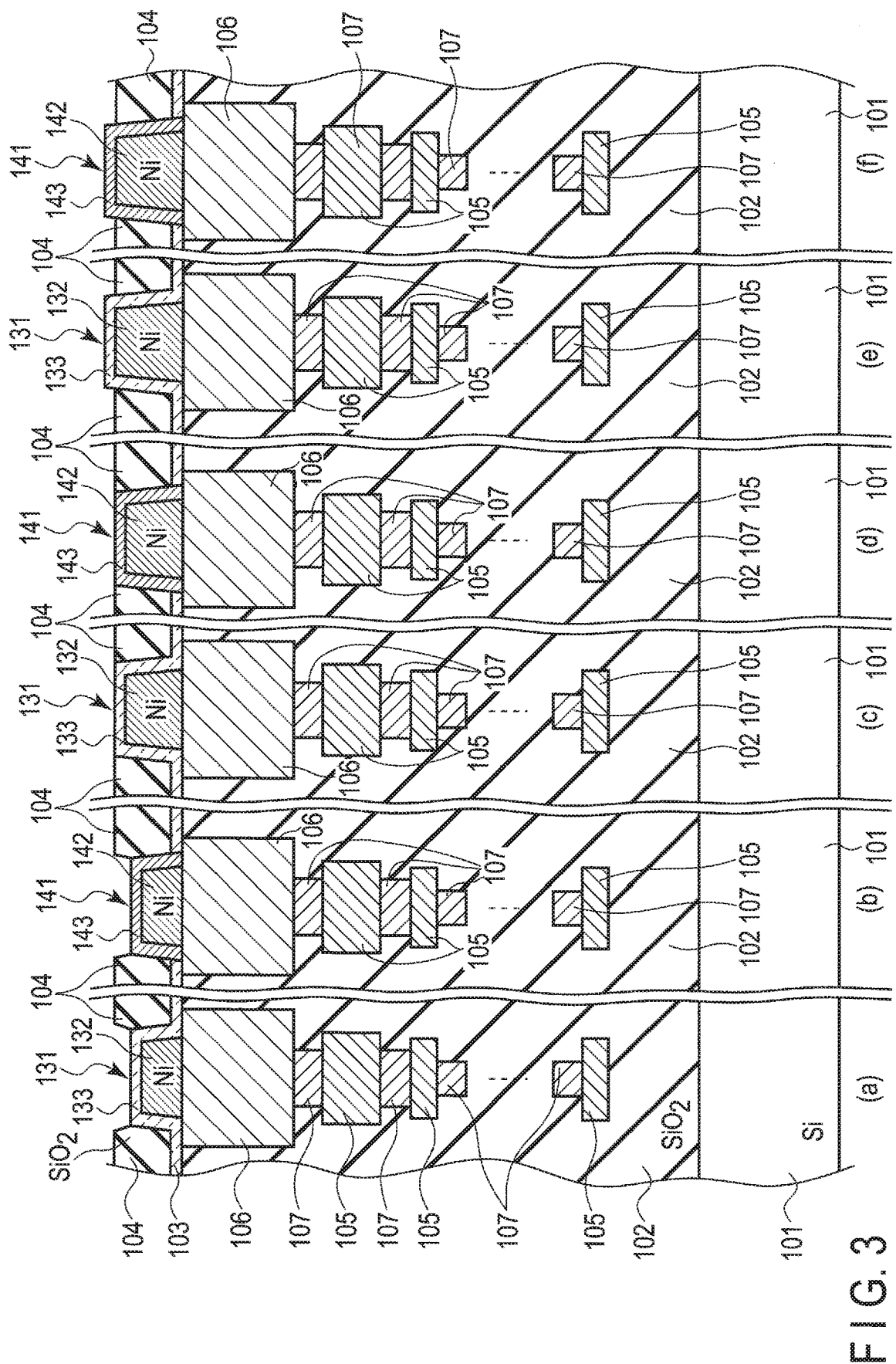
FIG. 3 is cross-sectional view showing an example of an electrode sensor pixel of the biosensor according to the embodiment.

FIGS. 2 and 3 are cross-sectional views of the sensor elements formed on the substrate of the biosensor. The substrate of the biosensor includes a plurality of pixels (sensor elements) which is divided by a lattice-shaped partition wall 104 formed of an insulating material and/or a resin on a semiconductor substrate 101. The biosensor includes a silicon substrate 101, a silicon oxide film 102 stacked and formed on the substrate 101, a silicon nitride film 103 formed on the surface of the silicon oxide film 102, and a portion formed on the surface of the silicon nitride film 103. The configuration may be such that the silicon nitride film 103 is not formed and the partition wall 104 is not directly formed on the interconnect 106 and the silicon oxide film 102. In the internal structure of the silicon oxide film 102, multilayer interconnects 105 are formed so as to be electrically connected to one another by a via 107 formed of a conductor material.

For example, in the partition wall 104 of FIG. 2, an ion concentration measuring pixel 111, a hydrogen ion concentration measuring pixel 121, a first sensor pixel 131 of a voltage signal, a second sensor pixel 141 of a current signal or a voltage signal, a first photosensor pixel 151, a second photosensor pixel 161, a third photosensor pixel 171, and a fourth photo pixel 181 are formed in the order of FIG. 2(a), FIG. 2(b), FIG. 2(c), FIG. 2(d), FIG. 2(e), FIG. 2(f), FIG. 2(g), and FIG. 2(h). The interconnects formed below the pixels are connected to a transistor (not shown). The transistor may be formed either on the substrate 101 located immediately below the pixel or around the detection region.

The ion concentration measuring pixel 111 includes an ion sensitive film 112 formed on the surface of the silicon nitride film 103. The ion sensitive film 112 contains, for example, polyvinyl chloride (PVC) as a base substance, and further contains an ionophore which selectively binds to a single type of ion, such as valinomycin, a plasticizer and an exclusion agent. Examples of the ionophore which binds to each ion are as follows: $Na^+$: bis(12-crown-4); $K^+$: bis (benzo-15-crown-5) or valinomycin; $Ca^+$: K23E1; and $NH_4^+$: TD19C6. The ion sensitive film may be formed by, for example, an inkjet printing method. The transistor connected to the ion concentration measuring pixel 111 detects changes in the ion concentration in the ion sensitive film 202.

In the above example, the ion concentration measuring pixel 111 is formed on the surface of the silicon nitride film 103. However, in place of the silicon nitride film, a silicon oxide film, an aluminum oxide film or a tantalum oxide film may be used, or the ion concentration measuring pixel 111 may be formed directly on the surface of the interconnect 106.

When the ion concentration measuring pixel 111 is formed, it is preferable to previously apply a voltage to the metal (electrode) disposed on the substrate 101 in a position facing an ink jet nozzle, i.e., position corresponding to the ion concentration measuring pixel 111. Thus, it is possible to allow the material (to be inkjet printed) to have directional properties and prevent the material from being discharged or splashed to an unintended region.

The hydrogen ion concentration measuring pixel 121 may use the silicon nitride film 103 as a hydrogen ion sensitive film. As the hydrogen ion sensitive film, a silicon oxide film, an aluminum oxide film or a tantalum oxide may be used in place of the silicon nitride film. In the hydrogen ion concentration measuring pixel 121, hydrogen ions are detected as the silanol group formed on the surface of the silicon nitride film 103 as a functional group. The transistor connected to the hydrogen ion concentration measuring pixel 121 detects changes in the ion concentration in the hydrogen ion concentration measuring pixel 121.

An electrical sensor pixel will be described with reference to FIGS. 2 and 3. The first sensor pixel 131 of a voltage signal includes, for example, an electrode 132 of a conductive material such as nickel, platinum, gold, titanium, a titanium compound, a conductive polymer or electrically conductive glass which is electrically connected to an interconnect 106 of an uppermost layer and a silicon nitride film 133 formed so as to cover the exposed surface of the electrode 132. Preferably, the silicon nitride film 133 has, for example, a thickness of 20 nm or less. The sensor pixel 131 may be produced by forming an electrode (pedestal) formed of nickel or the like on the surface of the interconnect 106 of the uppermost layer and depositing a silicon nitride film on the exposed surface of the electrode.

The sensor pixel 131 can detect an alternating current voltage signal based on the capacitive coupling between the electrode 132 and the silicon nitride film 133.

Further, it is possible to apply a voltage or a current to the electrode 132 via the interconnect 106. In other words, it is possible to electrically stimulate the target to be measured by using the electrode 132.

The second sensor pixel 141 of current signal or a voltage signal includes an electrode 142 of a conductive material such as nickel, platinum, gold, a titanium compound, a conductive polymer or electrically conductive glass which is electrically connected to an interconnect 106 of an uppermost layer and a conductor film 143 of platinum, gold, titanium, a titanium compound, a conductive polymer, electrically conductive glass or the like which is formed so as to cover the exposed surface of the electrode 142. The sensor pixel 141 may be produced by forming an electrode (pedestal) formed of platinum, gold, titanium, a titanium compound, a conductive polymer, electrically conductive glass or the like on the surface of the interconnect 106 of the uppermost layer and depositing a conductor film on the exposed surface of the electrode. By using nickel, titanium, a titanium compound, a conductive polymer or electrically conductive glass to form the electrode 142, it is possible to minimize the amount to use of a rare metal such as platinum or gold.

The sensor pixel 141 can detect a current signal and an alternating current voltage signal including a low frequency based on the conductance coupling between the electrode 142 and the conductor film 143.

Further, it is possible to apply a voltage or a current to the electrode 132 via the interconnect 106. In other words, it is possible to electrically stimulate the target to be measured by using the electrode 132.

The first sensor pixel 131 and the second sensor pixel 141, as shown in FIG. 3, may have any of a recess shape in which the top surface of the silicon nitride film 133 or the conductor film 143 is slightly hollowed from the top surface of the partition wall 104 (FIGS. 3(*a*) and (*b*)), a flat shape in which the top surface of the silicon nitride film 133 or the conductor film 143 is flush with the top surface of the partition wall 104 (FIGS. 3(*c*) and (*d*)), and a protrusion shape in which the top surface of the silicon nitride film 133 or the conductor film 143 is slightly protruded from the top surface of the partition wall 104 (FIGS. 3(*e*) and (*f*)). The transistor connected to the electrical sensor pixel may be in a region except for an IC chip.

The photosensor pixel will be described with reference to FIG. 2. A photodiode (light receiving element) 108 is formed in each portion of the silicon substrate 101 located immediately below each of the first to fourth photosensor pixels 151, 161, 171, and 181 (FIG. 2(*e*), FIG. 2(*f*), FIG. 2(*g*) and FIG. 2(*h*)). The interconnects 105 are not present immediately below the first to fourth photosensor pixels 151, 161, 171, and 181 so that the light from each of the photosensor pixels 151, 161, 171, and 181 can be received by the photodiode 108. The light from each of the other photosensor pixels is blocked by adjacent interconnects so that the light having a desired wavelength can be received.

The first photosensor pixel 151 includes an inorganic filter 152 formed on the lower surface of the silicon nitride film 103 and an organic filter 153 formed on the top surface of the silicon nitride film 103.

The inorganic filter 152 is, for example, a multilayer filter or a plasmon filter. The multilayer filter is a filter obtained by alternately depositing a low refractive material and a high refractive material. For example, a silicon oxide film may be used as the low refractive material, and zirconium dioxide or titanium oxide may be used as the high refractive material. As an example, it is preferable that the silicon oxide film has a thickness of 62±5 nm and zirconium dioxide has a thickness of 38±5 nm. These multilayer films can favorably reflect the light having a wavelength of 360±30 nm on the side of a wavelength of 510 nm. Specifically, a rejection ratio of 1/100000 can be obtained by stacking a pair of the two oxide films 30 times. The organic filter 603 may be formed of a pigment or a dye.

The first photosensor pixel 151 can transmit and absorb a specific wavelength because an optical filter having the inorganic filter 152 and the organic filter 153 is included. For example, in the fluorescence measurement, excitation light is removed and the transmitted fluorescence light is detected by the photodiode 108.

The first photosensor pixel 151 is applied when the number of layers required for the multilayer filter as the inorganic filter 152 is large. In other words, when the number of layers required for the inorganic filter 152 is large, it is necessary to make the height of the partition wall 104 higher in order to form the inorganic filter on the top surface of the silicon nitride film 103. This causes a structural defect. In such a case, the inorganic filter 152 is formed so as to be in contact with the lower surface of the silicon nitride film 103 so that the inorganic filter 152 can be formed in a necessary number of layers without making the height of the partition wall 104 higher.

The second photosensor pixel 161 includes an inorganic filter 162 that is formed on the top surface of the silicon nitride film 103 and an organic filter 163 that is formed on the surface of the inorganic filter 162 so as to be flush with the top surface of the partition wall 104.

The inorganic filter 162 and the organic filter 163 are the same or the like as those used in the first photosensor pixel 151.

The second photosensor pixel 161 can transmit and absorb a specific wavelength, similarly to the first photosensor pixel 151. For example, in the fluorescence measurement, excitation light is removed and the transmitted fluorescence light is detected by the photodiode 108.

The first photosensor pixel 151 is applied when the number of layers required for the multilayer filter as the inorganic filter 162 is small. In other words, when the number of layers required for the inorganic filter 162 is small, each of the inorganic filter and the organic filter 163 may be formed on the top surface of the silicon nitride film 103.

The silicon nitride film 103 in the first photosensor pixel 151 and the second photosensor pixel 161 may be replaced with a silicon oxide film. In the first place, the configuration of not forming the film is permitted.

In the third photosensor pixel 171, no filter is present on the top surface of the silicon nitride film 103. In the third photosensor pixel 171, an analysis target on the top surface of the silicon nitride film 103 is detected by the photodiode 108 using the visible light.

As for the third photosensor pixel 171, it is permitted that a silicon oxide or glass film is formed on the top surface of the silicon nitride film 103 so as to be flush with the top surface of the partition wall 104 in order to smooth a surface structure, similarly to each of the pixels.

The fourth photosensor pixel 181 includes a transparent electrode 182 that is embedded in the partition wall 104 and a via 183 that connects the interconnect 106 located immediately below the partition wall 104 to the transparent electrode 182.

The transparent electrode 182 is formed of a conductive oxide such as ITO, InGaZnO or $TiO_2$, or conductive glass.

The fourth photosensor pixel 181 apply a voltage to the transparent electrode 182 from the interconnect 106 through the via 183. Thereby the analysis target on the transparent electrode 182 is migrated, induced or subjected to electrical stimulation. The light emitted in such a state is detected by the photodiode 108. Alternatively, an electrical signal such as a voltage or potential of the analysis target may be measured, simultaneously with the detection of the light by the photodiode 108.

The method of forming the first photosensor pixel will be described with reference to FIG. 4.

The photodiode 108 is formed by doping impurities into the silicon substrate 101. Then, the interconnects 105 are formed while making the silicon oxide film 102 deposited (FIG. 4(a)).

Then, as shown in FIG. 4(b), the surface layer of the silicon oxide film 102 is selectively etched to form lattice-shaped protrusions 201. After that, as shown in FIG. 4(c), multilayer films 202 of an inorganic material are formed on the surface of the silicon oxide film 102 including the lattice-shaped protrusions 201, for example, by sputtering. Successively, the multilayer films 202 on the lattice-shaped protrusions 201 are selectively polished by chemical mechanical polishing (CMP) and the multilayer films are left between the lattice-shaped protrusions 201. As a result, a plurality of inorganic filters 152 is formed. Thereafter, the silicon nitride film 103 is deposited on the surface of the silicon oxide film 102 including the inorganic filters 152, for example, by a CVD method (FIG. 4(d)).

Then, as shown in FIG. 4(e), partition walls 104 formed of lattice-shaped protrusions of silicon oxide, similarly to the lattice-shaped protrusions 201, are formed by depositing a silicon oxide film on the surface of the silicon nitride film 103, for example, by the CVD method, and then patterning the silicon oxide film. Thereafter, the interior between the partition walls 104 is coated with an organic filter material so as to be flush with the surfaces of the partition walls 104 and the interior is dried. The organic filter 153 is stacked on each of the inorganic filters 152 through intermediary of the silicon nitride film 103. Thus, the first photosensor pixel 151 is formed (FIG. 4(f)). The resulting double-layered filters 152 and 153 are disposed so as to face the photodiode 108.

Here, the organic filter material may be applied by the inkjet printing method. At that time, similarly to the formation of the ion concentration measuring pixel 111, it is preferable to previously apply a voltage to the metal (electrode) disposed on the substrate 101 in a position facing an ink jet nozzle, i.e., position for forming the organic filter 153. Thus, it is possible to allow the material (to be inkjet printed) to have directional properties and prevent the material from being discharged or splashed to an unintended region.

Figure 5:
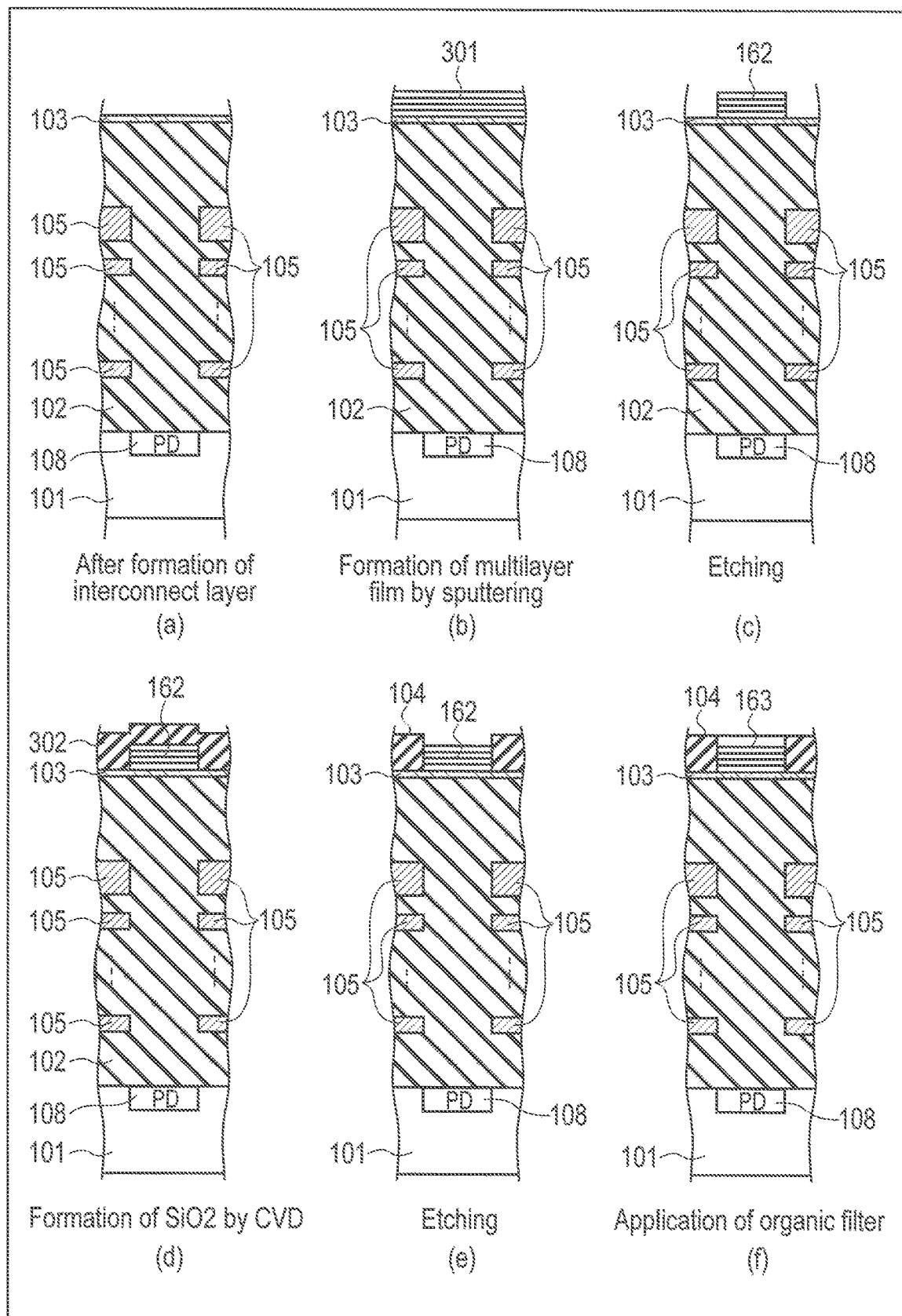
FIG. 5 is cross-sectional view showing an example of a production process of a photosensor pixel which is provided in the biosensor according to the embodiment.

The method of forming the second photosensor pixel will be described with reference to FIG. 5.

The photodiode 108 is formed by doping impurities into the silicon substrate 101. Then, the interconnects 105 are formed while making the silicon oxide film 102 deposited (FIG. 5(a)). Although FIG. 5(a) shows the case where the number of layers of the interconnects 105 is 3 or more, the number of layers can be 1 or 2.

Then, as shown in FIG. 5(b), a multilayer film 301 of an inorganic material is formed on the surface of the silicon nitride film 103, for example, by sputtering. Successively, the multilayer film 301 of an inorganic material is patterned to form a plurality of the inorganic filters 162 (FIG. 5(c)).

Then, as shown in FIG. 5(d), a silicon oxide film 302 having a thickness larger than that of the inorganic filters 162 is formed on the surface of the silicon nitride film 103 including a plurality of the inorganic filters 162. Then, as shown in FIG. 5(e), the silicon oxide film 302 on the inorganic filters 162 is removed selectively. And the partition walls 104 of lattice-shaped silicon oxide having a thickness larger than that of the inorganic filters 162 are formed on the surface of the silicon nitride film 103 so as to surround the inorganic filters 162. Thereafter, each of the surface of the inorganic filters 162 is coated with an organic filter material so as to be flush with the surfaces of the partition walls 104 and the surface is dried. Then, the organic filter 163 is stacked on each of the inorganic filters 162. Thus, the second photosensor pixel 161 is formed (FIG. 5(f)). The resulting double-layered filters 162 and 163 are disposed so as to face the photodiode 108.

The material of the interconnect 106 may be, for example, copper or aluminum, however it is not limited thereto.

The signals detected by the sensing units of the detection elements are sent, for example, from a transistor or a light receiving element to a portion of the circuit of the biosensor.

A temperature sensor pixel may include, for example, a transistor circuit including a plurality of field-effect transistors (FET), which uses a phenomenon in which the threshold potential of the FET is dependent on temperature. For example, an FET, a diode-connected FET which is series-connected to the FET, a series circuit including the FETs, and another FET are connected in parallel to one another to form a transistor circuit. It is possible to detect the temperature from the output voltage of the transistor circuit. Such a temperature sensor pixel may perform the temperature measurement at any of the above transistor forming portions of the semiconductor included therein. In that case, the temperature sensor pixel does not necessarily occupy the region of the surface of the biosensor. Alternatively, a configuration using the FETs may be disposed as an independent temperature sensor element.

In any of the sensor elements described above, organic and/or inorganic filters may be used in combination with each other. The filter to be used may be an optical filter such as a pigment or dye filter, or a combination thereof. Further, the frequency of the light passing through the filter may be selected as desired. The type, combination, and entire configuration of filter materials may be appropriately selected depending on a desired frequency. For example, all the sensor elements included in a biosensor may include any of the filters, or only some sensor elements may include any of the filters. When filters are included in a plurality of sensor elements, all the filters may be equal to or different from one another, or some of the filters may be equal to or different from one another.

Subsequently, the circuit configuration of the biosensor will be described with reference to the drawings.

Figure 6:
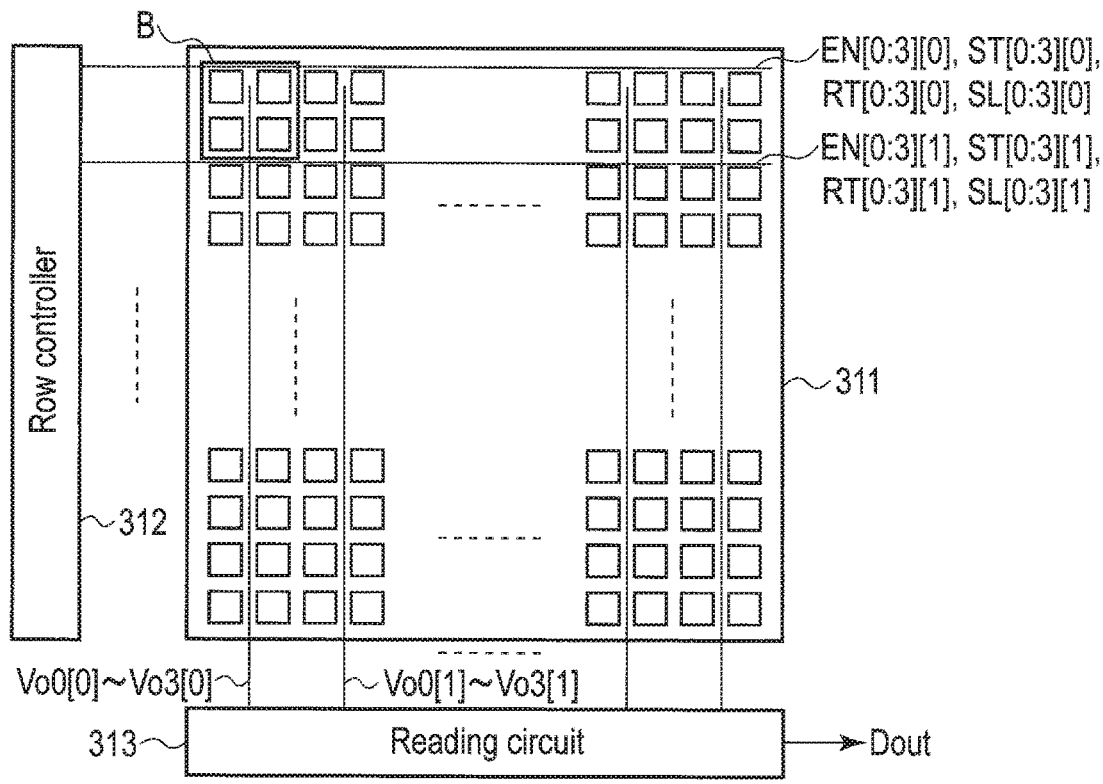
FIG. 6 is a schematic diagram showing an example of a circuit configuration of the biosensor according to the embodiment.
Figure 7:
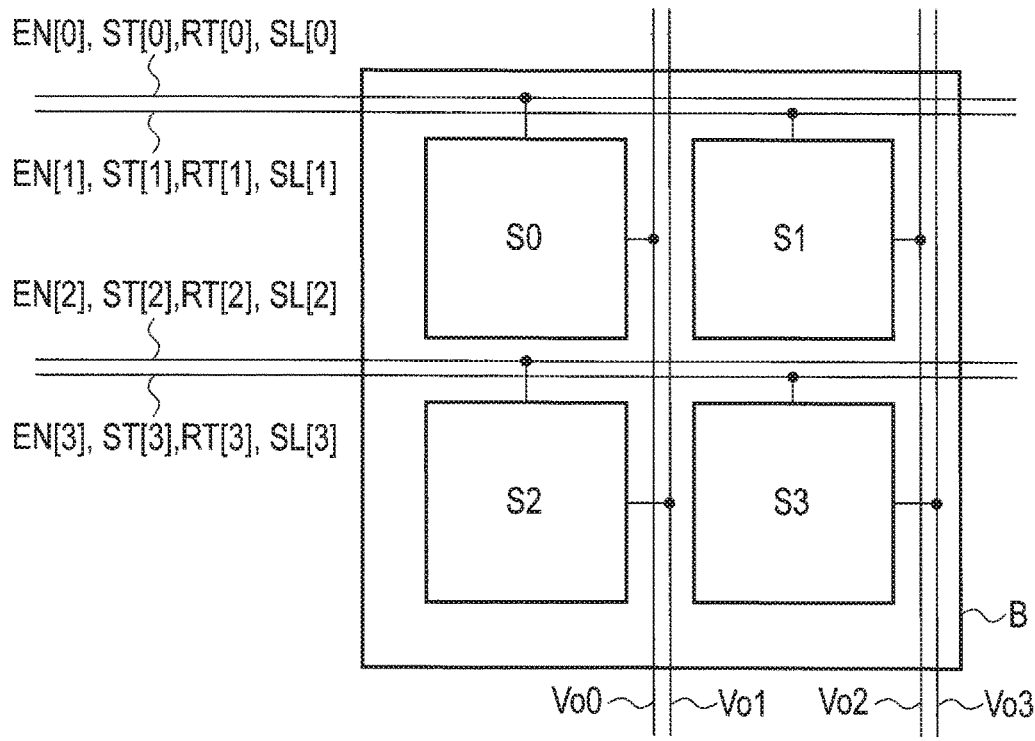
FIG. 7 is a circuit diagram showing an example of each subblock of the biosensor according to the embodiment.

FIGS. 6 and 7 show schematic examples of the circuit configurations of the biosensor according to the embodiment.

A biosensor 310 includes a sensor array 311, a row controller 312, and a reading circuit 313.

The sensor array 311 includes an array of a plurality of basic blocks. The basic blocks include, for example, mutually identical layouts and mutually identical circuit configurations. In this example, a basic block B311 includes four subblocks (pixels) S0, S1, S2, and S3. Each of the subblocks S0 to S3 is any one of the ion sensor, electrical sensor, and photosensor.

The row controller 312 controls the operation of detecting data on the pixels disposed in a matrix. For example, the row controller 312 controls the order of reading out the data from each of the subblocks (sensors).

For example, the row controller 312 generates an enable signal EN, a stimulus signal ST, a reset signal RT, and a transfer signal SL.

The enable signal EN, the stimulus signal ST, the reset signal RT, and the transfer signal SL are commonly supplied to a plurality of basic blocks arranged in a row direction. Here, the enable signal EN, the stimulus signal ST, the reset signal RT, and the transfer signal SL, which are supplied from the row controller 312, may be temporally different for each row. More specifically, the same signal pattern may be supplied to the next row at the timing delayed by a predetermined period after a signal pattern is supplied to a certain row.

In the enable signal EN [0:3] [i] (i=0, 1, . . . ), the stimulus signal ST [0:3] [i] (i=0, 1, . . . ), the reset signal RT [0:3] [i] (i=0, 1, . . . ), and the transfer signal SL [0:3] [i] (i=0, 1, . . . ) shown in FIG. 6, the number in the second parenthesis which is indicated by [i] (i=0, 1, . . . ) represents a row number. On the premise that temporally different signals per row are supplied, the number in the second parenthesis is omitted in FIG. 7 and the following description.

When the signals to be supplied to the basic block B are the enable signal EN [0:3] and the stimulus signal ST [0:3], the enable signal EN [0] and the stimulus signal ST [0] are supplied to a subblock S0 and the enable signal EN [1] and the stimulus signal ST [1] are supplied to a subblock S1. Further, the enable signal EN [2] and the stimulus signal ST [2] are supplied to a subblock S2. The enable signal EN [3] and the stimulus signal ST [3] are supplied to a subblock S3.

The reset signal RT [0:3] is a signal that resets the input voltage of an amplifier for amplifying a detection signal from a sensor. The transfer signal SL [0:3] is a signal that transmits the output signal of the amplifier to the reading circuit 313.

When the signals to be supplied to the basic block B are the reset signal [0:3] and the transfer signal SL [0:3], the reset signal RT [0] and the transfer signal SL [0] are supplied to the subblock S0, and the reset signal RT [1] and the transfer signal SL [1] are supplied to the subblock S1. Further, the reset signal RT [2] and the transfer signal SL [2] are supplied to the subblock S2, and the reset signal RT [3] and the transfer signal SL [3] are supplied to the subblock S3.

Each of the subblocks S0, subblocks S1, subblocks S2, and subblocks S3 outputs an output signal Vo0, an output signal Vo1, an output signal Vo2, and an output signal Vo3 to the reading circuit 313 respectively.

The number in parenthesis, as indicated by the output signal Vo0 [i] (i=0, 1, . . . ), the output signal Vo1 [i] (i=0, 1, . . . ), the output signal Vo2 [i] (i=0, 1, . . . ) or the output signal Vo3 [i] (i=0, 1, . . . ) as shown in FIG. 6, represents a column number. On the premise that the output signal is output to the reading circuit 313 for each column, the number in parenthesis is omitted in FIG. 7.

FIG. 8 to FIG. 13A and FIG. 13B show examples of subblock circuits. Each figure is an example of a sensor including one of the subblocks (sensors) S0 to S3 of FIG. 7. i represents any one of 0, 1, 2, and 3.

FIGS. 8 to 11 show an example when each of the subblocks is an ion sensor or an electrical sensor.

Each of the subblocks includes a switch element SW1 that applies a stimulus voltage Vs to an electrode Ei based on the stimulus signal ST[i], a switch element SW2 that resets an input of an amplifier B to a reset voltage VR based on the reset signal RT[i], a switch element SW3 that transmits the detection signal from the electrode Ei to the amplifier B based on the enable signal EN[i], and a switch element SW4 that validates an output signal Vo of the amplifier B based on the transfer signal SL[i].

As each of the switch elements SW1, SW2, SW3, and SW4, a P-channel type MOS transistor, an N-channel type MOS transistor or a CMOS switch including both the transistors may be used.

Further, as the amplifier B, a grounded source type amplifier, a grounded drain type amplifier or a differential amplification type amplifier may be used.

Figure 8:
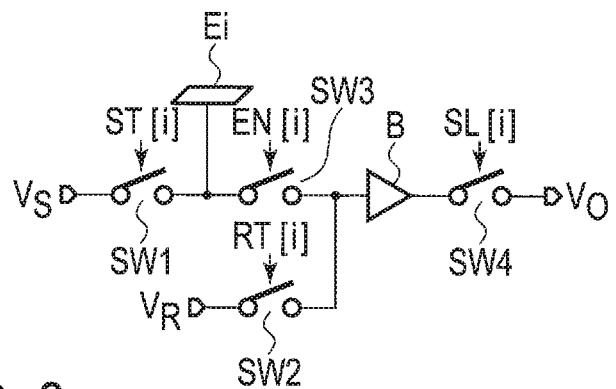
FIG. 8 is a circuit diagram showing an example of each subblock of the biosensor according to the embodiment.
Figure 9:
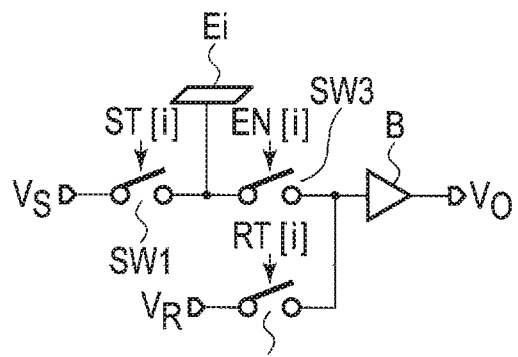
FIG. 9 is a circuit diagram showing an example of each subblock of the biosensor according to the embodiment.
Figure 10:
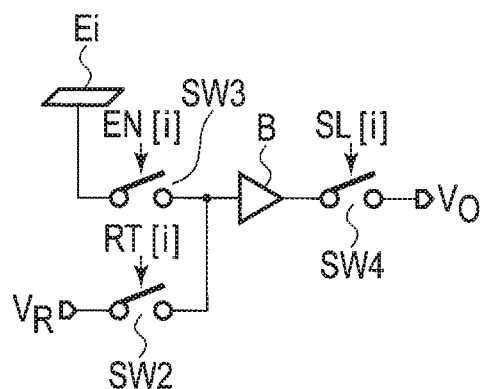
FIG. 10 is a circuit diagram showing an example of each subblock of the biosensor according to the embodiment.
Figure 11:
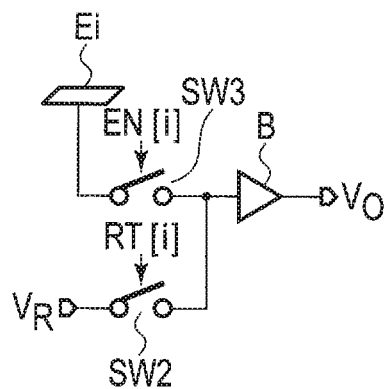
FIG. 11 is a circuit diagram showing an example of each subblock of the biosensor according to the embodiment.

FIG. 9 shows an example in which the switching element SW4 is omitted in the example of FIG. 8. FIG. 10 shows an example in which the switching element SW1 is omitted in the example of FIG. 8. FIG. 11 shows an example in which the switching elements SW1 and SW4 are omitted in the example of FIG. 8. In the subblocks of FIGS. 9 to 11, the same elements as the subblocks of FIG. 8 are denoted with the same reference numerals.

Figure 12:
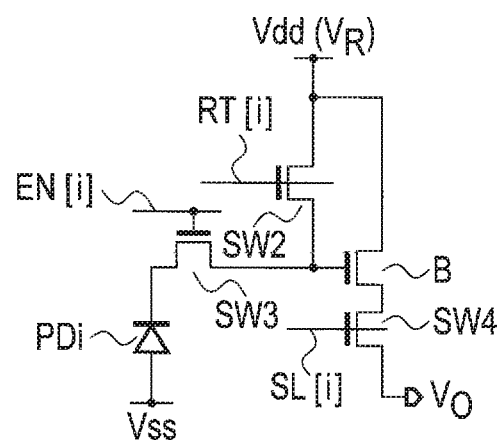
FIG. 12 is a circuit diagram showing an example of each subblock of the biosensor according to the embodiment.

FIG. 12 shows an example when each of the subblocks is a photosensor.

Each of the subblocks includes a switch element SW2 that resets an input of an amplifier B to a reset voltage VR, for example, a power supply voltage Vdd based on the reset signal RT[i], a switch element SW3 that transmits a detection signal from a photodiode (light receiving element) PDi to an amplifier B based on the enable signal EN[i], and a switch element SW4 that validates an output signal Vo of the amplifier B based on the transfer signal SL[i].

Figure 13A:
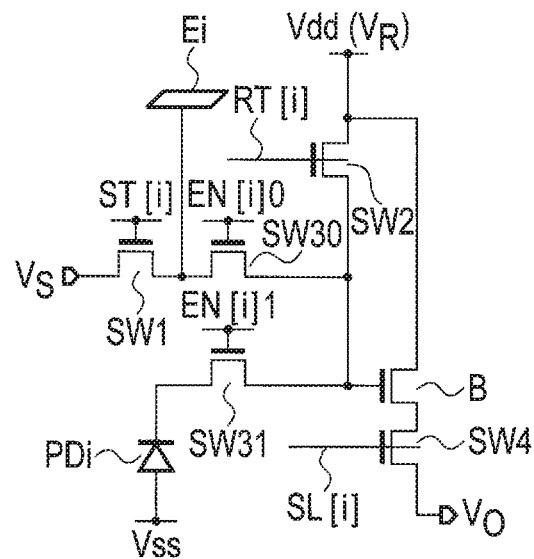
FIG. 13A is a circuit diagram showing an example of each subblock of the biosensor according to the embodiment.
Figure 13B:
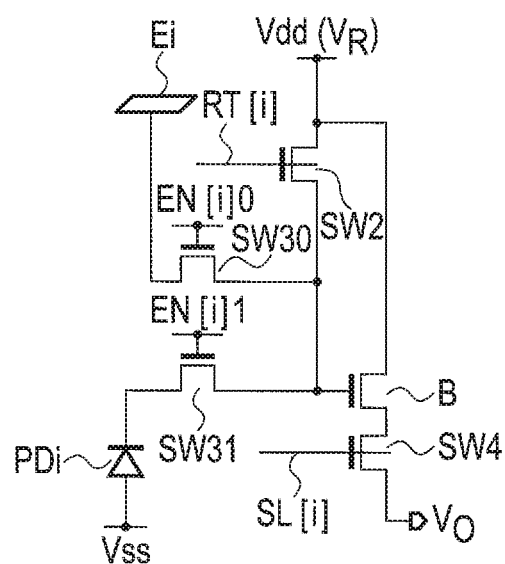
FIG. 13B is a circuit diagram showing an example of each subblock of the biosensor according to the embodiment.
Figure 15:
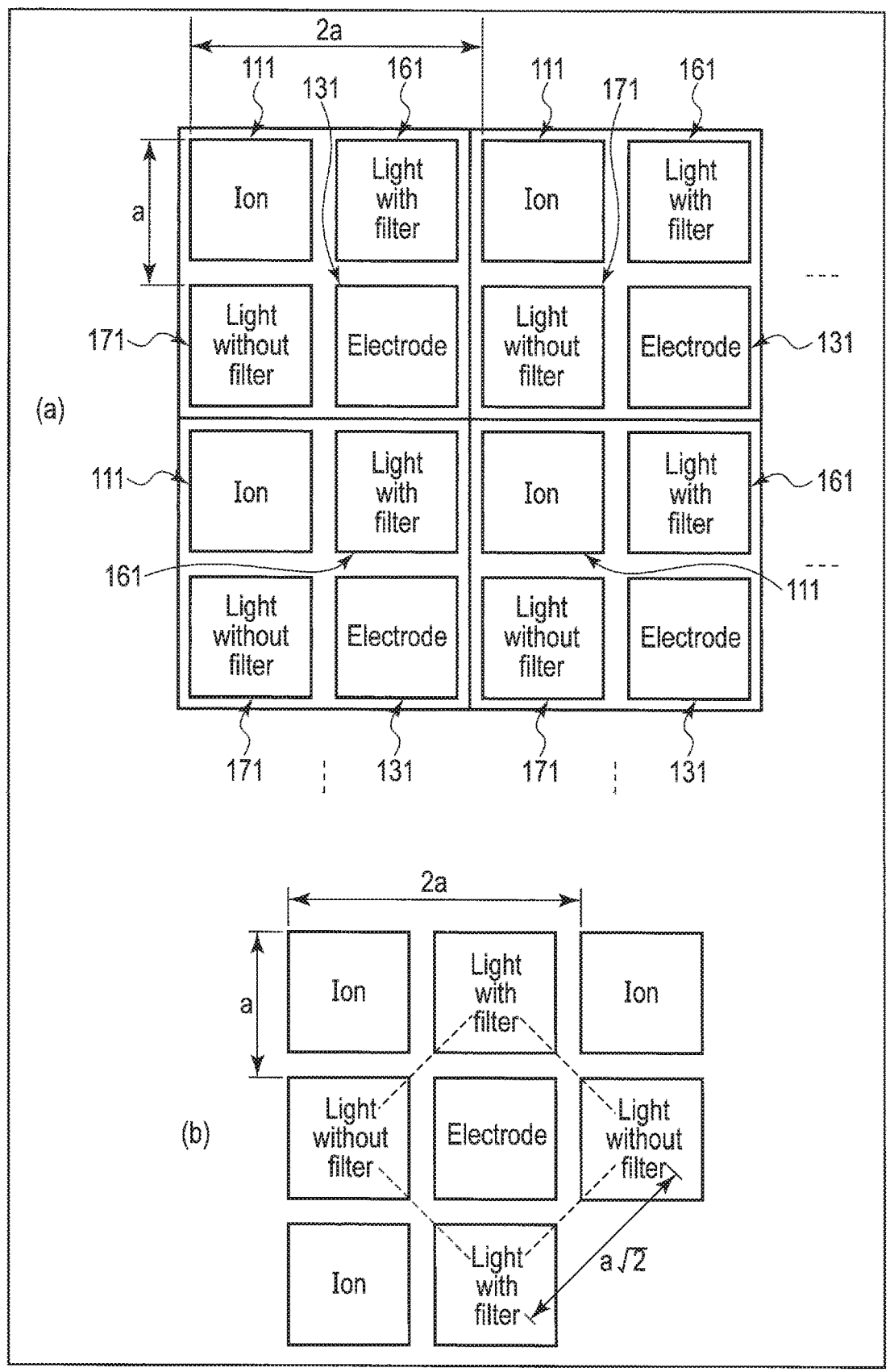
FIG. 15 is plan view showing an example of a sensor array according to an embodiment.

FIGS. 13A and 13B show an example when each of the subblocks is an overlay pixel.

The overlay pixel is a subblock obtained by combining an ion sensor or an electric sensor with a photosensor. For example, as described in the device structure, the overlay pixel is, for example, a structure in which the electrode Ei of the ion sensor or the electric sensor is overlapped with the photodiode PDi of the photosensor and the resulting product is stored in a subblock (pixel).

FIG. 13A is an example of the subblock which includes a function of electrically stimulate the detection target. Each of the subblocks includes a switch element SW1 that applies a stimulus voltage Vs to an electrode Ei based on the stimulus signal ST[i], a switch element SW2 that resets an input of an amplifier B to a reset voltage VR, for example, a power supply voltage Vdd based on the reset signal RT[i], a switch element SW30 that transmits a detection signal from an electrode Ei to the amplifier B based on the enable signal EN[i]0, a switch element SW31 that transmits a detection signal from a photodiode PDi to the amplifier B based on the enable signal EN[i]1, and a switch element SW4 that validates an output signal Vo of the amplifier B based on the transfer signal SL[i].

FIG. 13B is an example of the subblock which does not include a function of electrically stimulate the detection target. Each of the subblocks includes a switch element SW2 that resets an input of an amplifier B to a reset voltage VR, for example, a power supply voltage Vdd based on the reset signal RT[i], a switch element SW30 that transmits a detection signal from an electrode Ei to the amplifier B based on the enable signal EN[i]0, a switch element SW31 that transmits a detection signal from a photodiode PDi to the amplifier B based on the enable signal EN[i]1, and a switch element SW4 that validates an output signal Vo of the amplifier B based on the transfer signal SL[i].

FIG. 14 shows an example of a basic block circuit.

In this example, subblocks S0 to S3 in a basic block B11 have characteristics which share a switch element (reset transistor) SW2 that resets an amplifier B and a switch element SW4 that validates an output signal of the amplifier B.

The subblock S0 includes the electrode E0, a switch element SW10 that applies a stimulus voltage Vs to an electrode E0 based on the stimulus signal ST [0] and a switch element SW30 that transmits a detection signal from the electrode E0 to the amplifier B based on the enable signal EN [0].

The subblock S3 includes the electrode E3, a switch element SW13 that applies a stimulus voltage Vs to an electrode E3 based on the stimulus signal ST [3] and a switch element SW33 that transmits a detection signal from the electrode E3 to the amplifier B based on the enable signal EN [3].

When each of the subblocks S1 and S2 is an ion sensor or an electric sensor, the subblocks S1 and S2 include the same elements as those of the subblocks S0 and S3. When each of the subblocks S1 and S2 is a photosensor, the subblocks S1 and S2 include, for example, a photodiode PDi and a switch element SW3 in FIG. 12.

The basic block B11 further includes a switch element SW2 that resets an input of an amplifier B to a reset voltage VR based on the common reset signal RTcommon and a switch element SW4 that validates an output signal Vo of the amplifier B based on the common transfer signal SLcommon.

The order of reading out the data from each of the sensor elements by the circuit may be arbitrarily determined as desired depending on the type of the sensor element included in a biochip. For example, in the case of a biochip including a photosensor element, an electrical sensor element (e.g., a current or voltage signal sensor element), and a temperature sensor element, the read-out of these elements may be performed in this order or arbitrary order. The order and the time of read-out may be adjusted depending on the sensitivity of each of the sensor elements.

The above circuit may be connected to each sensor element as a reading control circuit that controls the read-out of a signal from each sensor element. Or a plurality of sensor elements may be connected to a circuit. Alternatively, the read-out of a signal may be performed by switching of a switch. Further, the reading control circuit may include a controller that controls the order of reading out a signal from a sensor element and an output circuit that outputs the signal from the sensor element to the outside of the circuit under control of the controller.

In addition to the reading control circuit that controls the read-out of a signal from each sensor element, the biosensor may include an analog-to-digital (A/D) conversion circuit as desired, when A/D conversion is necessary for the signal from the sensor element. Further, in addition to the reading control circuit, the biosensor may include a signal processing circuit that processes a signal from a sensor element in accordance with a previously set procedure. The signal processing circuit is also referred to as "a processing circuit" and performs, for example, time integration, auto-zeroing, chopping, correlated double sampling, and/or correlated multiple sampling. The biosensor may further include a communication circuit that transmits the result obtained in the processing circuit to the outside of the circuit, and may furthermore include a memory circuit that stores measurement conditions, measuring procedures, and mapping of samples and/or the obtained results, and a power circuit that supplies electricity to the biosensor on the substrate. The circuit included in the biosensor may be any of or a combination of the above circuits.

Subsequently, another configuration of the basic block will be described with reference to the drawings.

FIGS. 15 to 18 show several examples of the basic block. The basic block of FIG. 15($a$) is an example which includes four types of sensor elements, i.e., an example which includes the ion concentration measuring pixel 111, an electrode pixel 131, the photosensor pixel 161 having an optical filter, and the photosensor pixel 171 not having an optical filter. Similarly to the above example, the basic block includes four sensor elements of 2×2 matrix.

The biosensor including this basic block has the following characteristics. For example, when the target wavelength to be measured is a wavelength that transmits through the optical filter, both of two types of pixels which obtain light information (i.e., the photosensor pixel 161 having a filter and the photosensor pixel 161 not having a filter) can function as a sensor pixel. By disposing these pixels in a diagonal position, the spatial resolution of the light of the wavelength passing through the optical filter is increased by a factor of the square root of 2. In other words, assuming that one side of a sensor element is a, when the pitch between the optical filters is 2a, the effective pitch is a multiply by square root of 2 (FIG. 15($b$)). Further, the information obtained by the electrode sensor pixel 131 and the ion concentration measuring pixel 111 are respectively interpolated in the above manner using the information from the photosensor pixels 161 and 171 adjacent to these pixels, thereby improving the spatial resolution.

The basic block of FIG. 16 includes four types of sensor elements: a first ion concentration measuring pixel 111$a$ (Ion (A)), a second ion concentration measuring pixel 111$b$ (Ion (B)), a third ion concentration measuring pixel 111$c$ (Ion (C)), and a fourth ion concentration measuring pixel 111$d$ (Ion (D)).

According to the biosensor having this basic block, it is possible to simultaneously measure four types of ions. Further, it is possible to correct a nonspecific ion concentration response (i.e., a reaction by another ion that is not a detection target) using the known selectivity coefficient of ionophore of each type. Accordingly, the effective selectivity coefficient can be improved. Specifically, the concentration of each ion measured by each of plural types of ionophores is represented by the following formula: y=A·x wherein x is a true concentration vector of each ion, y is a concentration measurement vector of each ion, and A is a selectivity coefficient matrix.

In the case where there is an ionophore having ideal selectivity, the matrix A is a matrix having only a diagonal element, but the actual ionophore slightly responses to another type of ion. However, the selectivity coefficient matrix may be identified as known. Therefore, by calculating an inverse matrix $A^{-1}$ of the selectivity coefficient matrix and determining the inner product of the measured results, the concentration x of each ion can be obtained with high accuracy compared to when a single ionophore is measured: $x=A^{-1} \cdot y$.

Examples of the ion to be used as the analysis target include a hydrogen ion, a sodium ion, a potassium ion, a calcium ion, a chloride ion, an ammonium ion, however it is not limited thereto.

Figure 17:
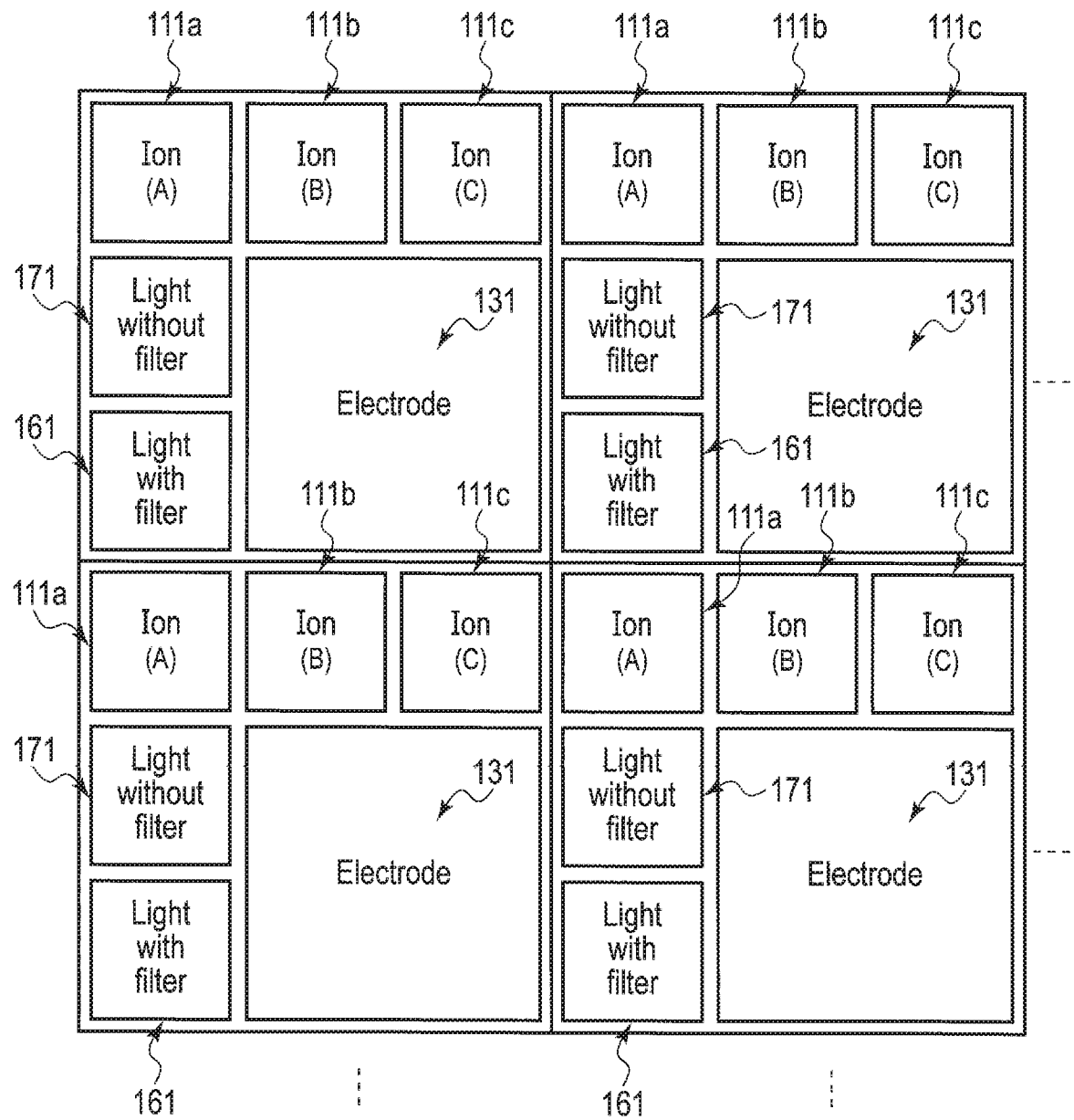
FIG. 17 is a plan view showing an example of a sensor array according to an embodiment.

The basic block of FIG. 17 includes six types of sensor elements, i.e., a first ion concentration measuring pixel 111a (Ion (A)), a second ion concentration measuring pixel 111b (Ion (B)), a third ion concentration measuring pixel 111c (Ion (C)), an electrode sensor pixel 131, a photosensor pixel 161 having a filter, and a photosensor pixel 171 not having a filter.

In the basic block, the electrode sensor pixel 131 has an area four times as large as that of each of the other four pixels. Two pixels are disposed along each of two sides of the electrode sensor pixel 131, and another pixel is disposed diagonally to the electrode sensor pixel 131 between the pixels.

The biosensor having this basic block is characterized in that six types of pixels are co-mounted. Further, the photosensor pixel 161 having a filter is placed adjacently to the photosensor pixel 171 not having a filter, thereby achieving sharing of the reading circuit. The first ion concentration measuring pixel 111a, the second ion concentration measuring pixel 111b, and the third ion concentration measuring pixel 111c are arranged in parallel, whereby the ion sensitive films of these pixels can be favorably formed. For example, simultaneous coating can be accomplished by using an ink-jet printer having ink jet heads that inject sensitive films of Ion (A), Ion (B), and Ion (C), thereby improving the production rate.

Further, the electrode sensor pixel is a pixel for which high sensitivity is most needed. For that reason, the area four times the area of each of the other pixels is allocated to the electrode sensor pixel. It is possible to increase the sensitivity of other pixels (e.g., the ion concentration measuring pixel and the photosensor pixel) by performing time integration by the processing circuit. However, in the case of the electrode sensor pixel, when the analysis target is a cell or the like, the time precision corresponding to a signal of 10 kHz is required for the action potential. Thus, it is not possible to perform time integration by the processing circuit. Therefore, high sensitivity is attained by enlarging the area of the sensing unit.

Figure 18:
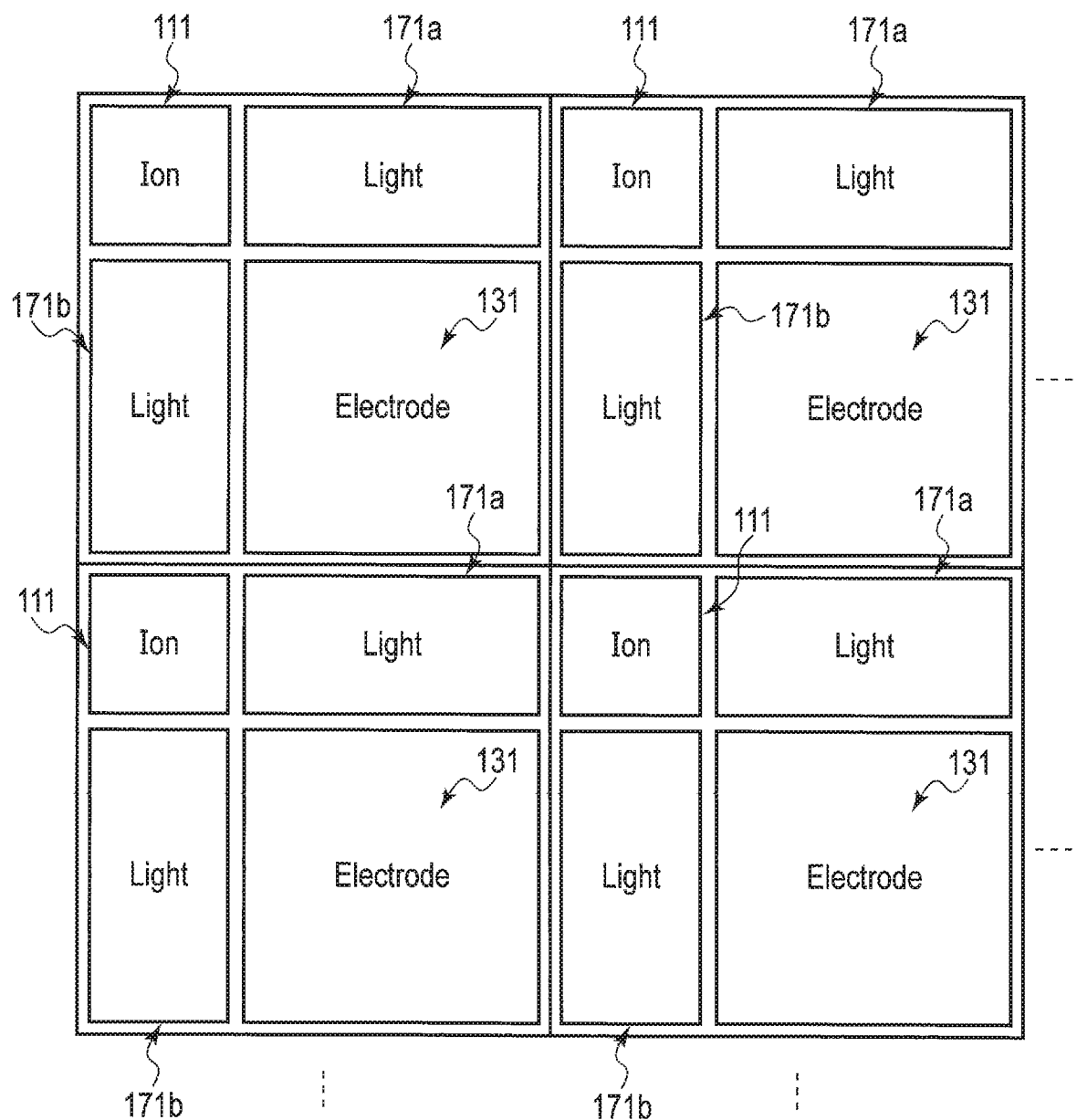
FIG. 18 is a plan view showing an example of a sensor array according to an embodiment.

The basic block of FIG. 18 includes an ion concentration measuring pixel 111, an electrode sensor pixel 131, and photosensor pixels 171a and 171b. Here, each of the photosensor pixels 171a and 171b has an area twice as large as that of the ion concentration measuring pixel 111. Similarly to FIG. 17, the electrode sensor pixel 131 has an area four times as large as that of the ion concentration measuring pixel 111. Photosensor pixels 171a and 171b are disposed along each of two sides of the electrode sensor pixel 131. Then, the ion concentration measuring pixel 111 is disposed diagonally to the electrode sensor pixel 131.

The biosensor having this basic block is characterized in that a plurality of the basic blocks is disposed in a regular matrix, and four sides of the electrode sensor pixel 131 are surrounded by the photosensor pixels 171a and 171b on the rectangle. A plurality of the photosensor pixels 171a and 171b surrounds the circumference, whereby it is possible to determine whether the analysis target is present on the electrode sensor pixel 131. In the basic block having such a structure, the length of the short side of the photosensor pixel 171 may be arbitrarily selected.

Examples of the embodiments are further shown in FIGS. 19 to 25. In these embodiments, a sensing unit used for light detection as a first sensing unit and a sensing unit used for electrode detection or another detection as a second sensing unit are disposed in a region. This is an example in which the structure allows for voltage application or sensing by the two sensing units in a pixel. The structure is referred to as "overlay structure".

Figure 19:
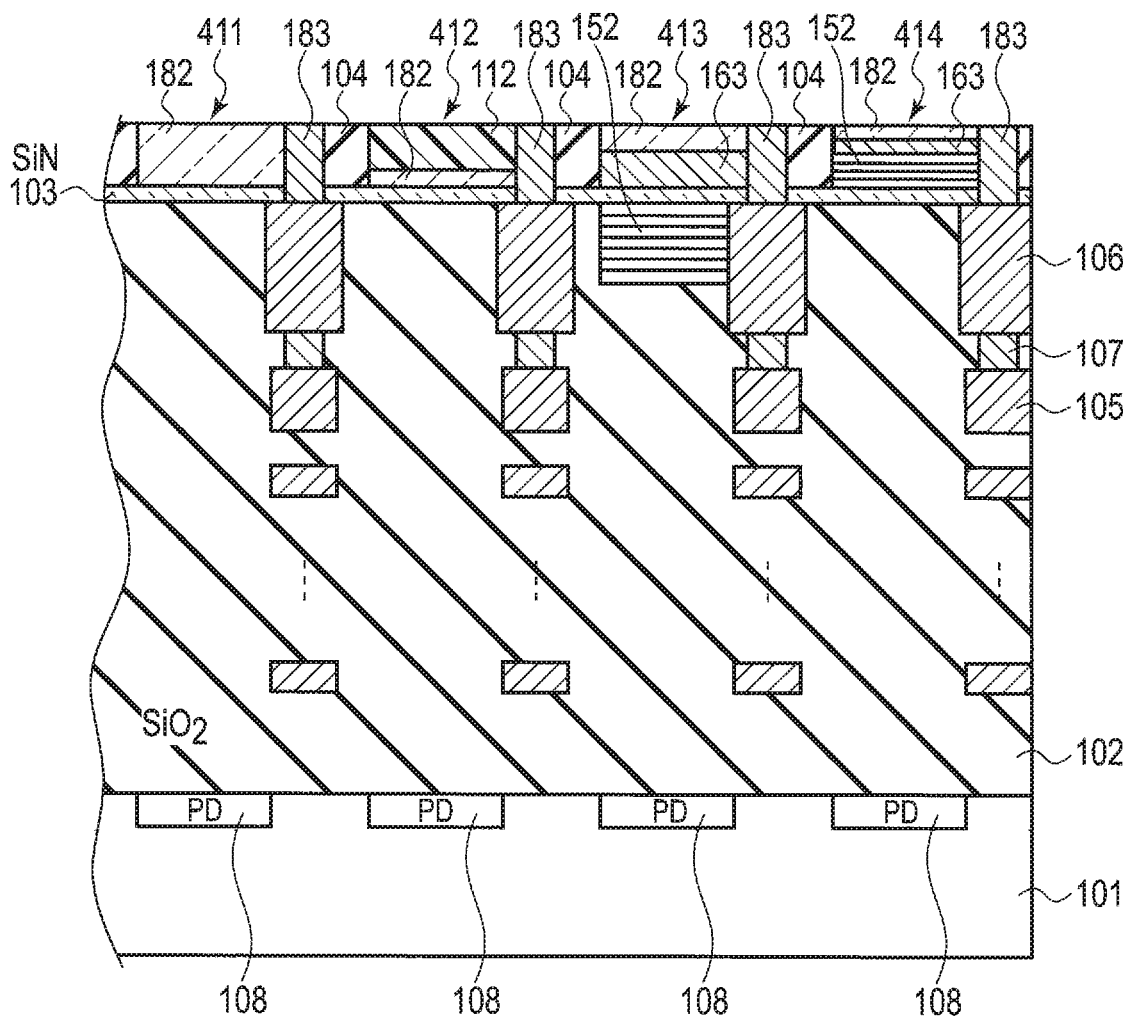
FIG. 19 is a cross-sectional view showing an example of a biosensor according to an embodiment.

FIG. 19 shows the section of the biosensor including the sensor pixel. The biosensor includes a plurality of pixels (sensor elements) which is divided by a lattice-shaped partition wall 104 formed of oxide silicon on a semiconductor substrate. The biosensor includes a silicon substrate 101, a silicon oxide film 102 stacked and formed on the substrate 101, a silicon nitride film 103 formed on the surface of the silicon oxide film 102, and a portion formed on the surface of the silicon nitride film 103. In the internal structure of the silicon oxide film 102, multilayer interconnects 105 are formed so as to be electrically connected to one another by vias formed of a conductor material.

For example, a first sensing unit 411 including an optical sensing unit and an electrode, a second sensing unit 412 including an optical sensing unit and a chemical substance sensing unit, a third sensing unit 413 including an optical sensing unit and a chemical substance sensing unit, a fourth sensing unit 414 including an optical sensing unit and a chemical substance sensing unit, in order from the left, are formed in the partition wall 104 of FIG. 19. The interconnects formed below the sensing units are connected to a transistor (not shown). The transistor may be formed either on the substrate 101 located immediately below the sensor pixel or around the sensing unit.

A conducting wall 183 is formed between one side of the lattice-shaped partition wall 104 and one side of the sensing unit 412, between one side of the lattice-shaped partition wall 104 and one side of the sensing unit 413, and between one side of the lattice-shaped partition wall 104 and one side of the sensing unit 414. The conducting wall 183 is connected to an interconnect layer including the interconnects 106 and 105. The conducting wall 183 may be formed of, for example, Pt, Ti, Au or the like.

A photodiode (light receiving element) 108 is formed in each portion of the silicon substrate 101 located immediately below each of the first to fourth sensing units 411 to 414. The interconnects 105 are not present immediately below the first to fourth sensing units 411, 412, 413, and 414 so that the light from each of the sensing units 411, 412, 413, and 414 can be received by the photodiode 108. In other words, the multilayer interconnects 105 prevent the light from the sensing units 411, 412, 413, and 414 from being leaked to and received by the adjacent photodiodes 108.

The sensing unit 411 has a transparent electrode 182. The sensing unit 412 includes a transparent electrode 182 and a chemical substance sensitive film 112 stacked on the transparent electrode. The sensing unit 413 includes an inorganic filter 152 formed so as to be in contact with the lower surface of the silicon nitride film 103, an organic filter 163 stacked on the top surface of the silicon nitride film 103, and a transparent electrode 182 on the top surface of the organic filter. The sensing unit 414 includes an inorganic filter 152 stacked on the top surface of the silicon nitride film 103, an organic filter 163 stacked on the top surface of the inorganic filter, and a transparent electrode 182 stacked on the top surface of the organic filter.

The signal from the transparent electrode 182 included in each of the first to fourth sensing units 411, 412, 413, and 414 passes through the interconnect 106 connected to a conductor 183 and is sent to a transistor (not shown) connected to a conductor 183.

In the first to fourth sensing units 411, 412, 413, and 414, a voltage is applied from the interconnect 106 to the transparent electrode 182 through the conductor 183. Thus, the analysis target on the transparent electrode 182 is migrated or induced or subjected to electrical stimulation. The light emitted in such as state is detected by the photodiode 108.

FIGS. 20(a) and (b) show an example of the embodiment in which a photosensor pixel and a conductor electrode are disposed in a pixel. FIG. 20(a) is a plan view of a biosensor, and FIG. 20(b) is a cross-sectional view of the biosensor. The biosensor includes insulating fence structures 104 that surround each of the pixels and a transparent conductive electrode (transparent electrode) 182 that is connected to the interconnect layer 105 by the conducting wall 183 with conductivity. The conducting wall 183 is formed so as to be adjacent to the lattice-shaped partition wall 104 and to be in contact with the lower surface of the transparent electrode 182. A micro lens (optical lens) 500 is stacked on the lower layer of the transparent electrode 182. A photodiode (light receiving element) 108 is formed in each portion of the silicon substrate 101 located immediately below each of the transparent electrodes 182. The interconnects 105 are not present immediately below the transparent electrodes 182 so that the light transmitted through each of the transparent electrodes 182 can be received by the photodiode 108. The fence structures 104 and the multilayer interconnects 105 prevent the light from each of the transparent electrodes 182 from being leaked to and received by the adjacent photodiodes 108.

The signal from the transparent electrode 182 passes through the interconnect 106 connected to the conductor 183 and is sent to a transistor (not shown) connected to the conductor 183.

In the case of the biosensor, a chemical substance sensitive film may be further formed on the upper layer of the transparent conductive electrode 182. Such a structure enables a pixel to have two types of functions. Thus, it is possible to increase the item without reducing the spatial resolution. Subsequently, an example of the embodiment which includes the chemical substance sensitive film on the upper layer of the transparent conductive electrode 182 will be described.

Figure 20:
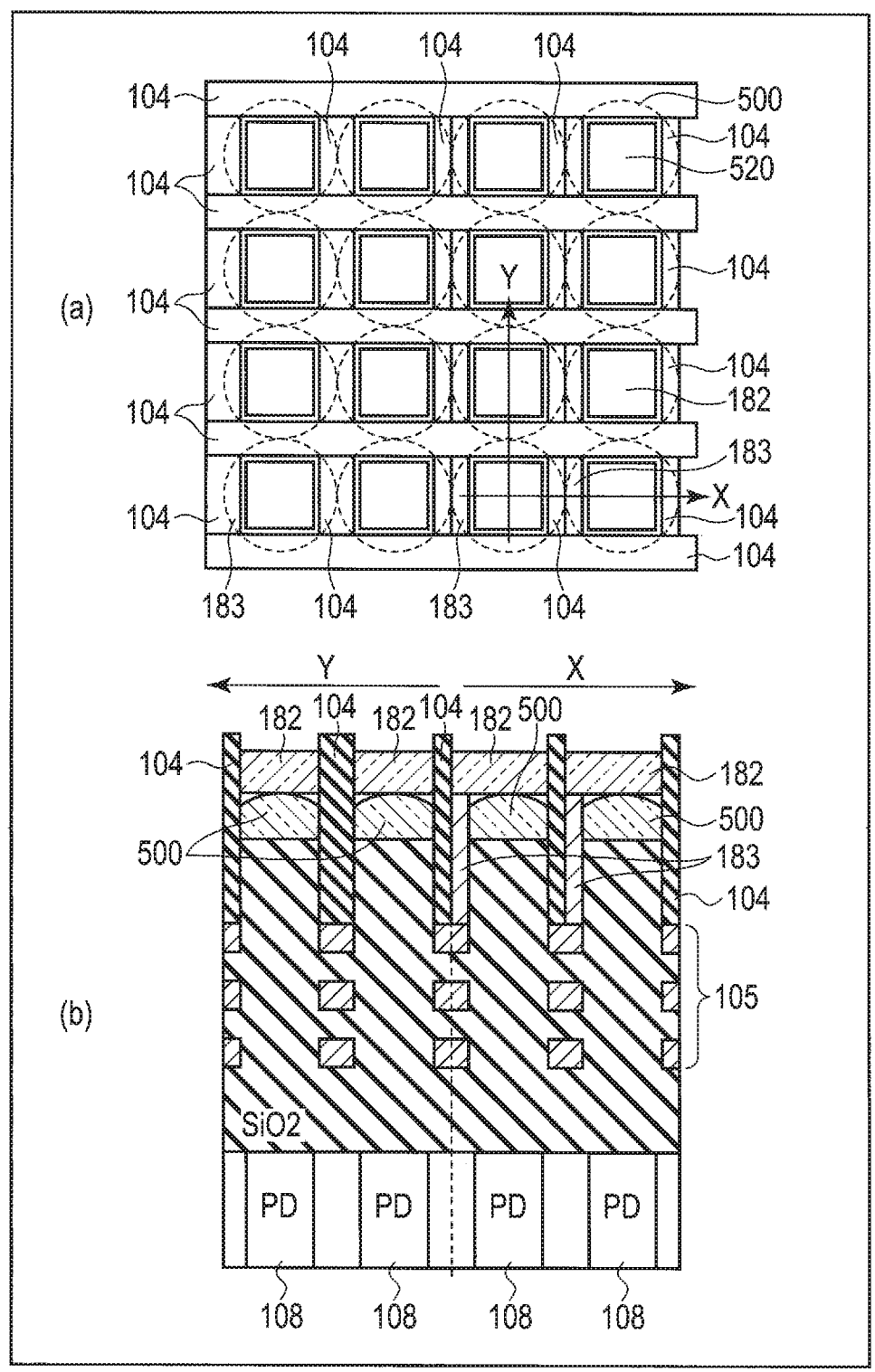
FIG. 20 is view showing an example of a biosensor according to an embodiment.
Figure 21:
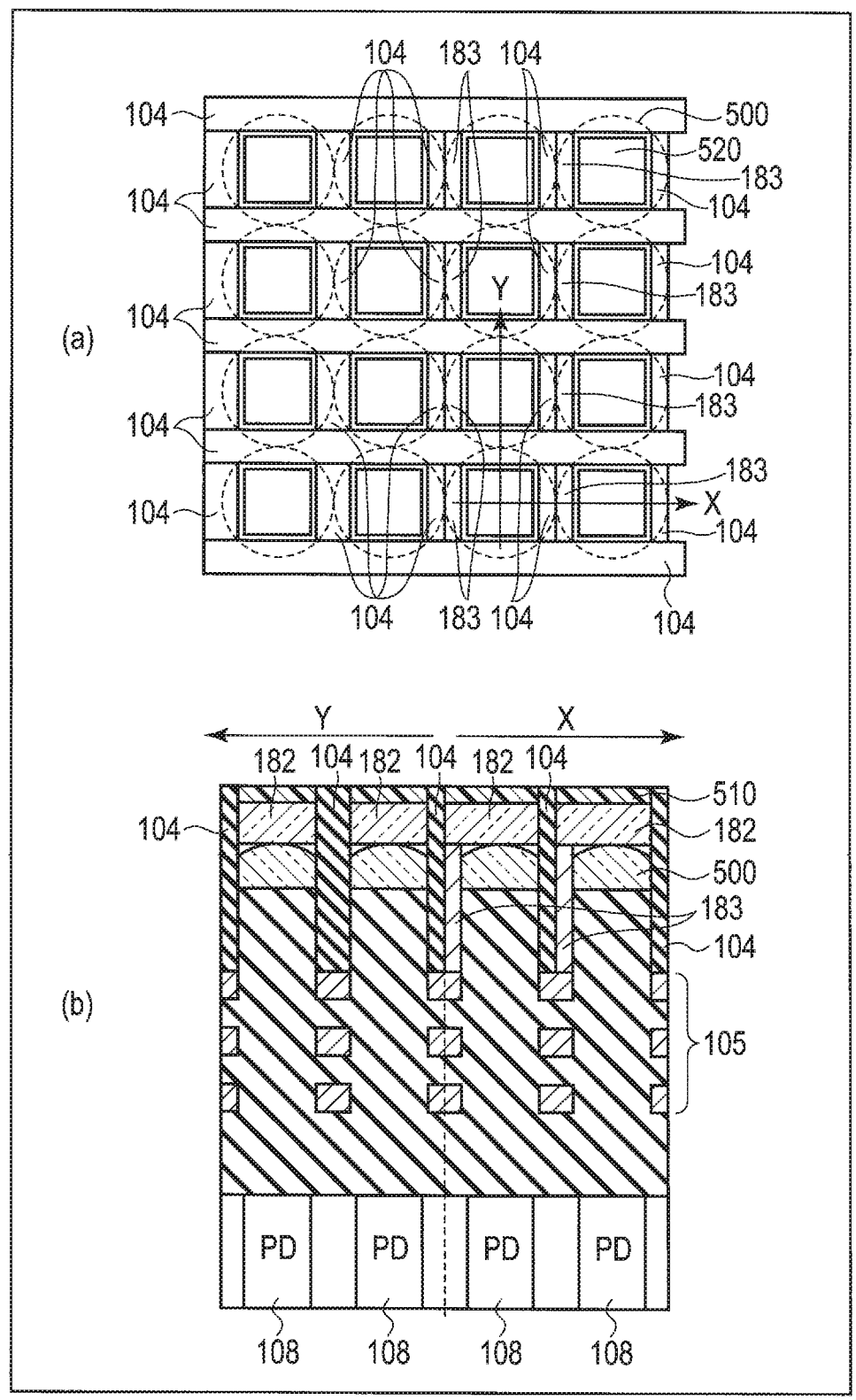
FIG. 21 is view showing an example of a biosensor according to an embodiment.

FIG. 21 shows an example of the embodiment in which an optical sensing unit and a chemical substance sensing unit stacked on the top surface of the optical sensing unit are disposed in a pixel. FIG. 21(a) is a plan view of a biosensor, and FIG. 21(b) is a cross-sectional view of the biosensor. This biosensor has the same structure as the biosensor of FIG. 20 except that the chemical substance sensing unit is further included.

Thus, a chemical substance sensitive film 510 is stacked on the transparent electrode 182 so that the concentration change of a specific chemical substance can be measured. For example, when silicon nitride is used as a sensitive film, the hydrogen ion concentration can be measured. The hydrogen ion sensitive film may be a silicon oxide film, an aluminum oxide film, a tantalum oxide film in place of the silicon nitride film. Alternatively, a polymer film containing an ionophore which specifically binds to a metal ion is used as the sensitive film, whereby the concentration of a specific metal ion can be measured. An example of a polymer film is a polyvinyl chloride film. Herein, the fence structure 104, which insulates the transparent electrode 182 from the adjacent pixel, is suitably effective in forming the chemical substance sensitive film 510. For example, in the case where the chemical substance sensitive film 510 is formed by the inkjet printing method, different coloring of the chemical substance sensitive films for every pixel allows for measurement of plural types of chemical substances. The end of the interconnect 105 is connected to a measuring circuit (not shown), whereby the concentration change of the chemical substance is sensed as an electrical signal. The measuring circuit may be located near each of the pixels or may be located around a pixel sensing region.

Figure 22:
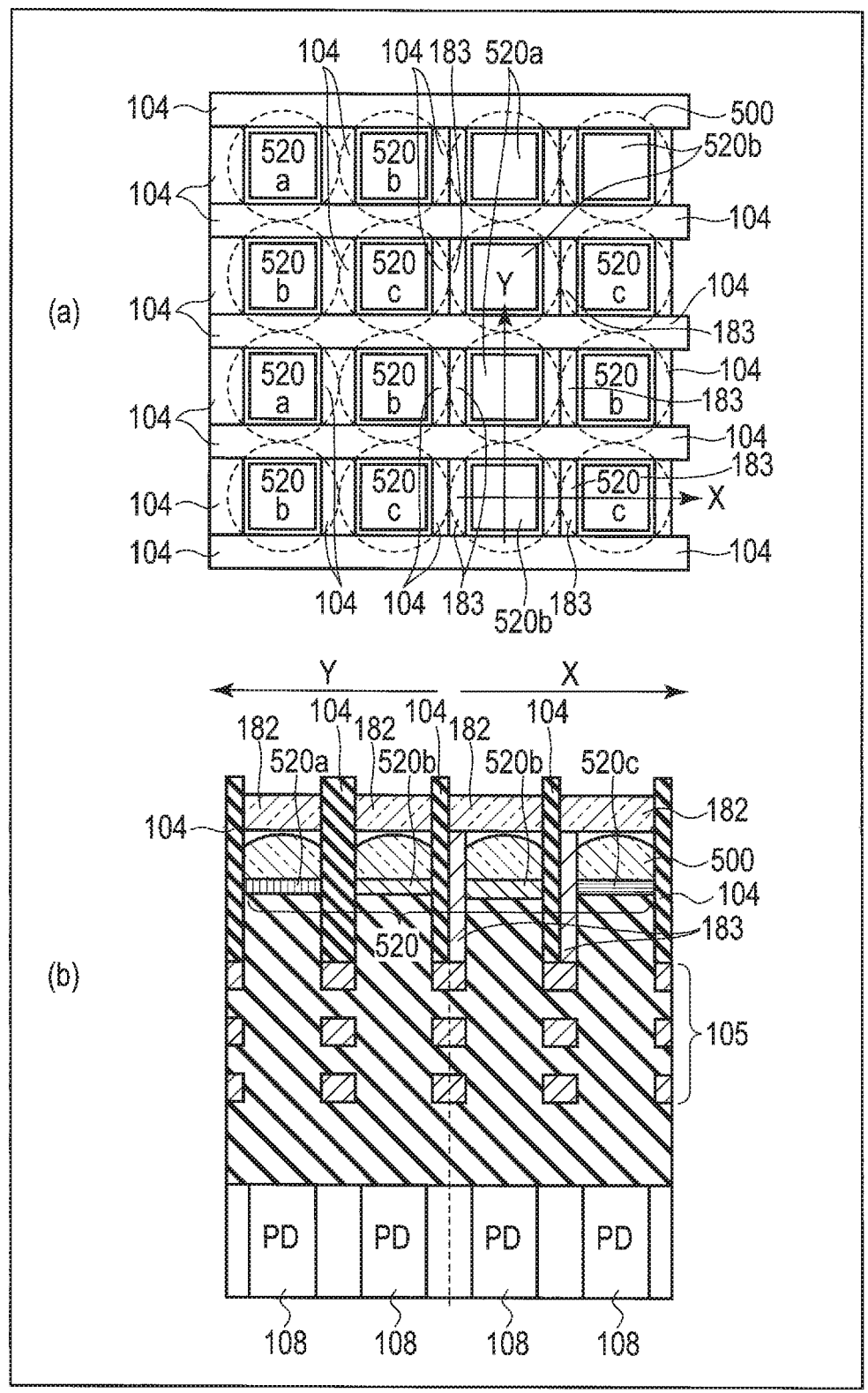
FIG. 22 is view showing an example of a biosensor according to an embodiment.

FIG. 22 shows an embodiment in which the biosensor shown in FIG. 20 further includes an optical filter 520 on the lower surface of the micro lens (optical lens) 500.

In this embodiment, the use of the optical filter 520 allows a specific wavelength to be absorbed by the optical filter 520 and allows a specific wavelength to transmit through the transparent electrode 182 and the photodiode 108. The optical filter 520 may be an organic filter or an inorganic filter or a combination thereof. The organic filter may be, for example, a filter obtained by using a pigment or dye. The inorganic filter may be, for example, a multilayer filter or a plasmon filter. The multilayer filter of the inorganic filter may be formed on the lower surface of the silicon nitride 103 or may be formed on the top surface of the silicon nitride 103. It is difficult to increase the level of the lattice-shaped partition wall 104 by oxide silicon. Accordingly, when the number of layers required for the multilayer film is large, it is preferable that the multilayer film is embedded in the lower surface of the silicon nitride 103. When the number of layers is small, it is preferable that the multilayer film is embedded in the lower surface of the silicon nitride 103. The multilayer filter may be, for example, a multilayer filter obtained by alternately stacking oxide silicon and zirconium dioxide. A silicon oxide film has a thickness of 62±5 nm and a zirconium dioxide film has a thickness of 38±5 nm so that the films can favorably reflect the light having a wavelength of 360 nm±30 nm with reference to a wavelength of 510 nm. These films are preferred. Specifically, a rejection ratio of 1/100000 can be obtained by stacking a pair of the two oxide films 30 times. For example, these optical filters may be used in order to remove excitation light and transmit fluorescence light in the fluorescence measurement.

The circuit configurations in the embodiments which have the overlay structures as shown in FIGS. 20 to 22 will be described with reference to FIGS. 23 to 25.

Figure 23:
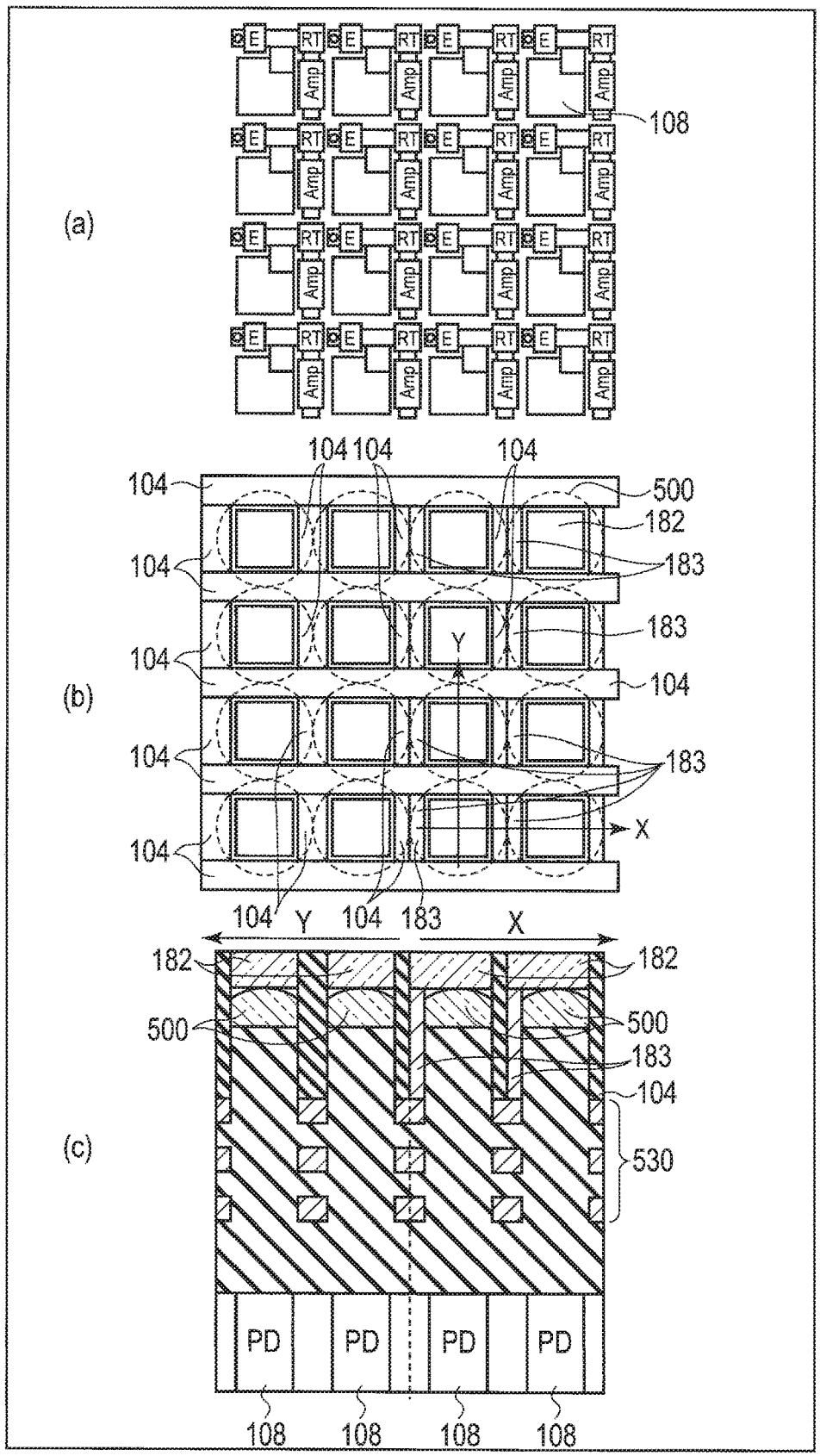
FIG. 23 is view showing an example of a biosensor according to an embodiment.

FIG. 23 shows an example of a circuit configuration which may have the almost same structure as that of the biosensor shown in FIG. 20. FIG. 23(a) is a plan view showing a circuit configuration, FIG. 23(b) is a plan view showing a structure corresponding to the circuit configuration, and FIG. 23(c) is a cross-sectional view of the structure.

The biosensor includes insulating fence structures 104 that surround each of the pixels and a transparent conductive electrode (transparent electrode) 182 that is connected to the interconnect layer 105 by the conducting wall 183 with conductivity. The conducting wall 183 is formed so as to be adjacent to one side of the lattice-shaped partition wall 104 and to be in contact with the lower surface of the transparent electrode 182. A micro lens (optical lens) 500 is stacked on the lower layer of the transparent electrode 182. A photodiode (light receiving element) 108 is formed in each portion of the silicon substrate 101 located immediately below each of the transparent electrodes 182. The interconnects 105 are not present immediately below the transparent electrodes 182 so that the light from each of the transparent electrodes 182 can be received by the photodiode 108. It is preferable that the insulating fence structures 104 have a light blocking effect. This case prevents the light from each of the transparent electrodes 182 from being leaked to and received by the adjacent light receiving elements 108. The materials of the transparent electrode are as described above.

In this biosensor, circuit portions may be formed on the light receiving element 108 and the transparent electrode 182, respectively. FIG. 23(a) is an overview of an example of the circuit which is connected to the light receiving element 108 and disposed. This example is an example of 1V1H. A circuit is disposed for every pixel and the circuit includes an amplifier (Amp), a first switch element (E), and a second switch (RT). The circuit may be configured similarly to, for example, the circuit configuration shown in FIG. 13A or 13B.

The biosensor may further have any of the chemical substance sensitive films on the upper layer of the transparent conductive electrode 182. The height of the fence structure 104 is made higher than the top surface of the transparent electrode 182, thereby preventing the leakage to the circumference caused by applying a material of the chemical substance sensitive film.

Thus, according to the overlay structure, it is possible to increase the item without reducing the spatial resolution.

Figure 24:
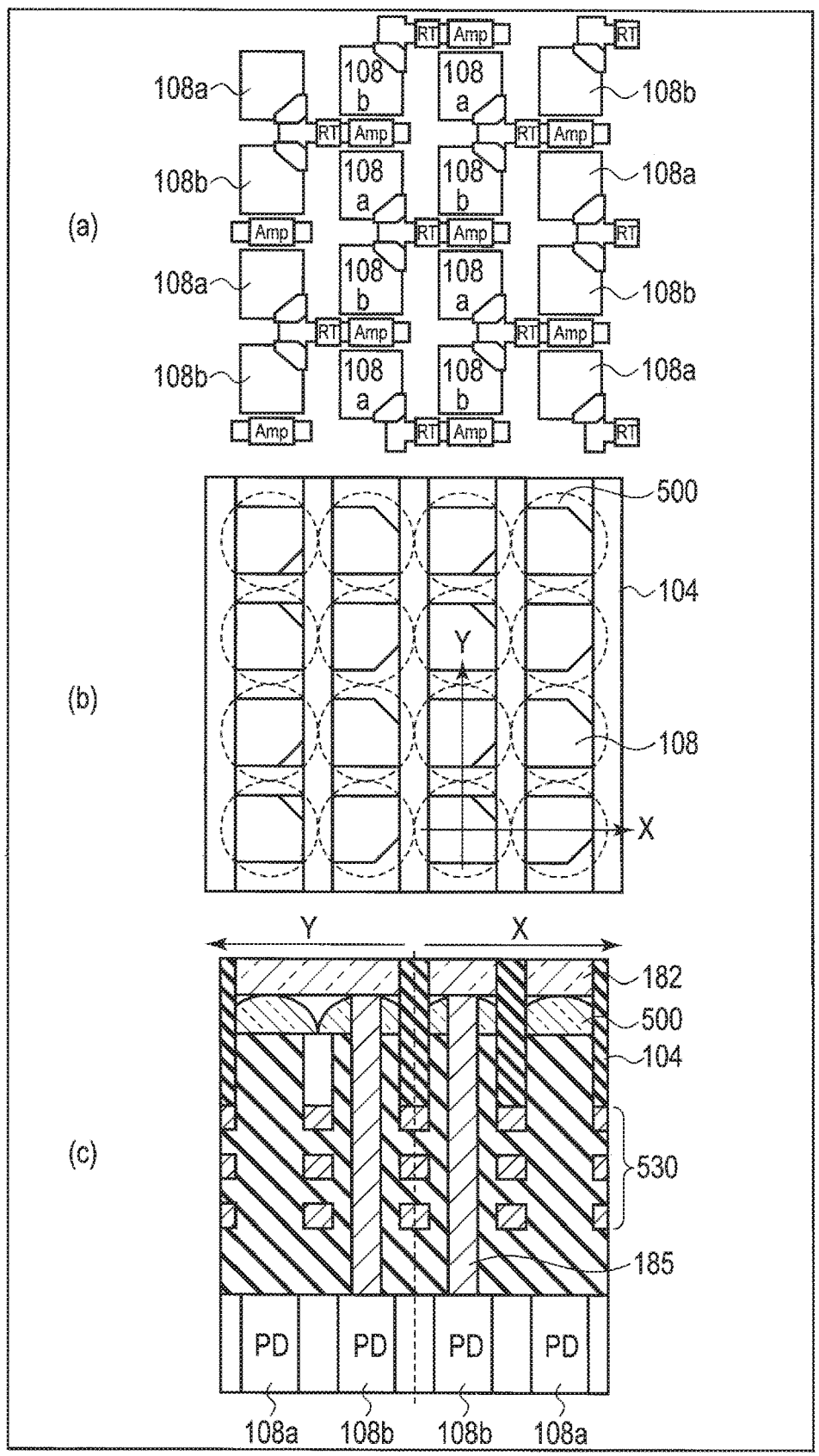
FIG. 24 is view showing an example of a biosensor according to an embodiment.

FIGS. 24 to 25 show another example of a circuit which shares the adjacent pixel and the reading circuit.

FIG. 24 is an example when sharing the reading circuit by two pixels in a vertical direction. In the case of this biosensor, two vertically adjacent detection pixels or two horizontally adjacent detection pixels have different structures to each other. The first sensor pixel is a photosensor pixel (i.e., the photosensor element) that senses only the light. The second sensor pixel is a sensor pixel that senses the light and senses the electricity. In this sensor element, a trench via 185 in the structure of the biosensor shown in FIG. 20 is not disposed so as to be adjacent to one side of the lattice-shaped partition wall 104, but is formed so as to be in contact with the lower surface of the transparent electrode 182 in the center of the detection element. A photodiode (light receiving element) 108 is formed in each portion of the silicon substrate 101 located immediately below each of the transparent electrodes 182, and the trench via 185 is extended and connected to the light receiving element 108. In the circumference of the trench via 185, the light from the transparent electrode 182 reaches a light receiving element 108a so that the light receiving element 108a can receive the light. Meanwhile, a light receiving element 108b is shielded by the trench via 185, whereby it does not serve as the light receiving element any more, but functions as a terminal that is electrically connected to the transparent electrode 182.

The reading circuit is shared by two vertically adjacent pixels, i.e., the first sensor pixel and the second sensor pixel. Such a zigzag mode may be obtained by remodeling an existing widely-used image sensor product. In this case, it is advantageous because the preceding step (FEOL) does not need to be changed.

FIG. 25 is another example when sharing the reading circuit by two pixels in a vertical direction. This biosensor has a sensor pixel that senses the light and senses the electricity. In this sensor element, a trench via 185 in the structure of the biosensor shown in FIG. 20 is not disposed so as to be adjacent to one side of the lattice-shaped partition wall 104, but is disposed in the position corresponding to one side of the lattice-shaped partition wall 104 so as to be replaced with one side of the partition wall 104. The trench via 185 is formed so as to be in contact with the lower surface of the transparent electrode 182. In the case of the overlay mode, an electrode switch Tr. (E) is added in the FEOL step, thereby achieving a fully stacked structure.

In any modes as shown in FIGS. 24 and 25, a selection transistor may further added to the pixel circuit. In the biosensor, the upper layer or the lower layer of a transparent member or the transparent electrode 182 may include an optical filter such as a color filter.

In the embodiment that senses the light described herein, the micro lens is arbitrary. The micro lens may be removed from the embodiment that includes the micro lens or the micro lens may be added to the embodiment that does not include the micro lens.

Although the examples of two vertically adjacent pixels are described above, the reading circuit may be shared among a plurality of pixels, in any of the modes, such as horizontally adjacent pixels (1V2H), vertically and horizontally adjacent pixels (2V2H), and a plurality of pixels in a vertical or horizontal direction (e.g., 4V1H, 4V2H).

In the embodiment which includes the transparent electrode 182, a function for adding a voltage or current to the transparent electrode 182 may be included. In the case of the configuration, for example, a switch Tr. (F) that controls the connection to the transparent electrode 182 may be provided. Further, the switch may be connected to the amplifier. Applying a voltage or current allows the analysis target on the transparent electrode to be electrically stimulated while measuring the optical image. It is useful to observe a change of the analysis target before and after stimulation. Further, applying a voltage or current to the transparent electrode 182 allows for performing electrophoresis or dielectrophoresis while measuring the optical image.

Such a structure allows for simultaneously performing plural measurements, detection e.g., pH sensing, detection of a chemical substance, concentration measurement, measurement of a current or voltage, measurement of a potential, measurement of a potential change, observation of light, measurement of a fluorescence intensity and/or measurement of a temperature, and further allows for simultaneously performing electrical stimulation, electrophoresis or dielectrophoresis.

Specific examples of at least three types of sensor elements included in the biosensor according to the embodiment are shown below. At least three types of the sensor elements may be selected so as to have different functions. For example, even if the same three chemical sensor elements are selected, when the chemical substances to be detected are different, they are three types of sensor elements;

(1) a chemical sensor element in which the sensing portion includes a chemical substance sensitive film;

(2) a pH sensor element in which the sensing portion includes a hydrogen ion sensitive film;

(3) a metal ion concentration sensor element in which the sensing unit includes a metal ion sensitive film;

(4) an electrode sensor element in which the sensing portion includes a metal layer and an insulating layer stacked on the metal layer;

(5) an electrode sensor element in which the sensing portion includes a first metal layer and a second metal layer stacked on the metal layer;

(6) a photosensor element in which the sensing portion includes at least double-layered inorganic optical filter layer, and at least a single-layered organic optical filter layer that is stacked upward on the inorganic optical filter layer;

(7) a photosensor element in which the sensing portion includes a light-transmissive member and a light receiving element that receives light passed through the light-transmissive member;

(8) a photoelectric sensor element in which the sensing portion includes a transparent electrode and a light receiving element that receives light passed through the transparent electrode;

(9) a chemical substance-electrical sensor element in which the sensing portion includes a transparent electrode and a chemical substance sensitive film stacked on the transparent electrode;

(10) an electrical-photosensor element in which the sensing portion includes at least a single-layered organic optical filter layer and/or at least a double-layered inorganic optical filter layer, and the transparent electrode; and

(11) an electrical-photosensor element in which the sensing portion includes at least a double-layered inorganic optical filter layer, at least a single-layered organic optical filter layer that is stacked above the inorganic optical filter layer, and the transparent electrode that is stacked above the organic optical filter layer.

The term "analysis target" used herein may be either a substance to be detected or a substance to be analyzed. For example, the analysis target may be an animal-derived sample such as a biological tissue section, an isolated cell, a cultured cell, a cultured tissue, a cell membrane, an antibody, blood, plasma, serum, urine, stool, and mucosa. Or, the analysis target may be an environment-derived sample such as a plant, soil, river, lake, and atmosphere. Further, microorganisms such as viruses, bacteria, and parasites may be used as samples. Or, the analysis target may be a chemical substance that includes a bio-related substance such as nucleic acid, protein, acetylcholine or dopamine or may be any of ions such as $H^+$, $K^+$, $Na^+$, $Ca^{2+}$, $Fe^{2+}$, $Fe^{3+}$, $Cu^{2+}$, $Cl^-$, and $SO^{4-}$.

The biosensor according to the embodiment can efficiently examine a plurality of test items (i.e., multiple items) on any analysis targets.

The biosensor enables the potential change, ionic behavior, secretion analysis, and morphology observation of tissue sections, cultured cells or the like to be favorably and simultaneously examined.

The biosensor according to the embodiment is not limited thereto, and utilized in various fields including physiology, pharmacology, biology, and iatrology. As a matter of course, it is possible to use the biosensor according to the embodiment in fields other than the field of biotechnology.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A biosensor comprising:
   a substrate; and
   a sensor matrix in a two-dimensional region on the substrate, wherein;
   the sensor matrix comprises a plurality of basic blocks each of which comprises at least three sensor elements, each sensor element having a sensing unit and obtaining different information,
   one of the at least three sensor elements is a first electrical-photosensor element, and
   the first electrical-photosensor element comprises a transparent electrode and a light receiving element which is disposed at a surface of the substrate which is located immediately below the transparent electrode.

2. The biosensor of claim 1, wherein the sensing units face a surface of the biosensor and the sensor matrix forms a sensor pixel array as a whole.

3. The biosensor of claim 1, wherein the sensor elements other than the first electrical-photosensor element comprise at least one of:
   (1) a chemical substance photosensor element including a transparent electrode, a light receiving element which is located on the substrate immediately below of the transparent electrode, and a chemical substance sensitive film stacked on the transparent electrode;
   (2) a second electrical-photosensor element in which the sensing unit includes at least a single-layered organic optical filter layer and/or at least a double-layered inorganic optical filter layer, and the transparent electrode;
   (3) a third electrical-photosensor element in which the sensing unit includes at least a double-layered inorganic optical filter layer, at least a single-layered organic optical filter layer that is stacked upward on the inorganic optical filter layer, and the transparent electrode that is stacked upward on the organic optical filter layer;
   (4) a chemical sensor element in which the sensing unit includes a chemical substance sensitive film;
   (5) a pH sensor element in which the sensing unit includes a hydrogen ion sensitive film;
   (6) a metal ion concentration sensor element in which the sensing unit includes a metal ion sensitive film;
   (7) a first electrode sensor element in which the sensing unit includes a metal layer and an insulating layer stacked on the metal layer; and
   (8) a second electrode sensor element in which the sensing unit includes a first metal layer and a second metal layer stacked on the metal layer.

4. The biosensor of claim 1, further comprising a first circuit portion on the substrate, wherein the first circuit portion reads out a signal from the sensor elements by a type of the sensor elements.

5. The biosensor of claim 4, further comprising a second circuit portion on the substrate, wherein the second circuit portion reads out a detection signal from each of the sensor elements.

6. The biosensor of claim 5, wherein the first or second circuit portion comprises a controller which controls an order of reading out in turn signals from the at least three sensor elements, and an output circuit which outputs in turn the signals from the at least three sensor elements to outside of the biosensor under the control of the controller.

7. The biosensor of claim 5, further comprising an A/D conversion circuit, a signal processing circuit, a communication circuit, a memory circuit and/or a power circuit on the substrate, which are connected to the first circuit portion or the second circuit portion.

8. The biosensor of claim 4, wherein the first circuit portion comprises a controller which controls an order of reading out in turn signals from the at least three sensor elements, and an output circuit which outputs in turn the signals from the sensor element to outside of the biosensor under the control of the controller.

9. The biosensor of claim 4, further comprising an A/D conversion circuit, a signal processing circuit, a communication circuit, a memory circuit and/or a power circuit on the substrate, which are connected to the first circuit portion.

10. The biosensor of claim 1, wherein a size of each of the sensor elements ranges from 300 nm×300 nm to 20 μm×20 μm.

11. The biosensor of claim 1, wherein the light receiving element receives light transmitted through the transparent electrode that is located immediately above the light receiving element.

12. The biosensor of claim 1, wherein the transparent electrode contacts an analysis target which is being detected or analyzed by the biosensor.

* * * * *